(12) United States Patent
Kitaoka et al.

(10) Patent No.: US 12,263,239 B2
(45) Date of Patent: Apr. 1, 2025

(54) EXTERNAL COMPOSITION CONTAINING ASCORBIC ACID AND/OR SALT THEREOF

(71) Applicant: ROHTO PHARMACEUTICAL CO., LTD., Osaka (JP)

(72) Inventors: Yu Kitaoka, Osaka (JP); Masatoshi Haga, Osaka (JP)

(73) Assignee: ROHTO PHARMACEUTICAL CO., LTD., Osaka (JP)

( * ) Notice: Subject to any disclaimer, the term of this patent is extended or adjusted under 35 U.S.C. 154(b) by 491 days.

(21) Appl. No.: 16/958,389

(22) PCT Filed: Dec. 27, 2018

(86) PCT No.: PCT/JP2018/048188
§ 371 (c)(1),
(2) Date: Jun. 26, 2020

(87) PCT Pub. No.: WO2019/131892
PCT Pub. Date: Jul. 4, 2019

(65) Prior Publication Data
US 2021/0052481 A1 Feb. 25, 2021

(30) Foreign Application Priority Data
Dec. 27, 2017 (JP) .................. 2017-252208

(51) Int. Cl.
*A61K 8/67* (2006.01)
*A61K 8/34* (2006.01)
(Continued)

(52) U.S. Cl.
CPC .............. *A61K 8/676* (2013.01); *A61K 8/345* (2013.01); *A61K 8/416* (2013.01); *A61Q 19/02* (2013.01); *A61Q 19/08* (2013.01)

(58) Field of Classification Search
CPC .. A61P 17/00; A61P 43/00; A61P 1/00; A61P 19/02; A61P 27/02; A61P 29/00; A61P 17/06; A61P 1/04; A61P 31/00; A61P 31/10; A61P 31/16; A61P 31/04; A61P 35/00; A61P 37/06; A61P 31/12; A61P 9/00; A61P 25/00; A61P 25/28; A61P 17/02; A61P 37/00; A61P 3/00; A61P 33/02; A61P 37/08; A61P 1/12; A61P 25/16; A61P 3/06; A61P 3/08; A61P 31/14; A61P 31/22; A61P 25/18; A61P 25/30; A61P 37/02; A61P 1/16; A61P 11/06; A61P 17/16; A61P 17/18; A61P 13/02; A61P 13/08; A61P 13/12; A61P 17/10; A61P 19/00; A61P 19/06; A61P 3/04; A61P 3/10; A61P 31/06; A61P 31/08; A61P 31/18; A61P 31/20; A61P 33/04; A61P 33/06; A61P 33/10; A61P 33/12; A61P 33/14; A61P 35/02; A61P 35/04; A61P 37/04; A61P 39/06; A61P 7/02; A61P 9/08; A61P 9/10; A61P 11/00; A61P 19/08; A61P 25/04; A61P 25/14; A61P 27/04; A61P 3/02; A61P 7/06; A61P 9/04; A61K 45/06; A61K 2300/00; A61K 9/0014; A61K 9/0019; A61K 31/167; A61K 47/10; A61K 48/00; A61K 31/5377; A61K 47/32; A61K 47/38; A61K 9/0031; A61K 9/10; A61K 9/1635; A61K 2039/53; A61K 39/39; A61K 31/506; A61K 31/52; A61K 48/0066; A61K 8/0241; A61K 2039/545; A61K 2039/55555; A61K 31/7048; A61K 31/7105; A61K 38/00; A61K 39/12; A61K 39/145; A61K 39/155; A61K 8/0208; A61K 9/0053; A61K 9/1271; A61K 9/5123; A61K 9/5146; A61K 31/485; A61K 8/345; A61K 2800/56; A61K 31/17; A61K 31/282; A61K 31/337; A61K 31/4178; A61K 31/505; A61K 31/513; A61K 31/635; A61K 31/655; A61K 31/675; A61K 31/704; A61K 31/7068; A61K 31/7076; A61K 33/243;
(Continued)

(56) References Cited

U.S. PATENT DOCUMENTS 6,495,148 B1 12/2002 Abbiati
2019/0151284 A1 5/2019 Haga et al.

FOREIGN PATENT DOCUMENTS

CN 1660081 A 8/2005
EP 2 818 157 A1 8/2013
(Continued)

OTHER PUBLICATIONS

JP2004331629 translation, "Morimoto". (Year: 2004).*
(Continued)

*Primary Examiner* — Audrea B Coniglio
(74) *Attorney, Agent, or Firm* — Meunier Carlin & Curfman LLC

(57) ABSTRACT

The present invention provides an external composition superior in stability and use feeling. According to the present invention, an external composition is prepared which includes (A) at least one selected from the group consisting of an ascorbic acid and an ascorbic salt, (B) a diol having 3 carbon atoms, (C) at least one selected from the group consisting of a low-molecular-weight betaine, an organic acid salt, an inorganic acid salt, a basic amino acid, a basic amino acid salt, 3-O-ethylascorbic acid, and a 3-O-ethylascorbic acid salt, and (D) water, and a content of ethoxydiglycol of said composition is less than 30 mass %.

10 Claims, No Drawings

(51) Int. Cl.
*A61K 8/41* (2006.01)
*A61Q 19/02* (2006.01)
*A61Q 19/08* (2006.01)

(58) Field of Classification Search
CPC ........ A61K 47/14; A61K 8/553; A61K 8/676; A61K 9/1617; A61K 9/48; A61K 9/70; A61K 9/7007; A61K 31/10; A61K 31/43; A61K 31/431; A61K 31/437; A61K 36/53; A61K 47/08; A61K 48/005; A61K 48/0075; A61K 8/9789; A61K 31/375; A61K 36/484; A61K 8/41; A61K 31/395; A61K 31/4155; A61K 31/519; A61K 31/685; A61K 31/7115; A61K 36/746; A61K 47/26; A61K 8/44; A61K 8/64; A61K 9/08; A61K 31/424; A61K 31/454; A61K 31/4706; A61K 36/54; A61K 36/752; A61K 36/85; A61K 36/87; A61K 47/186; A61K 8/361; A61K 8/416; A61K 8/4946; A61K 8/60; A61K 8/602; A61K 2039/505; A61K 2800/28; A61K 2800/30; A61K 2800/412; A61K 2800/651; A61K 2800/782; A61K 31/131; A61K 31/135; A61K 31/198; A61K 31/401; A61K 31/405; A61K 31/416; A61K 31/4172; A61K 31/7052; A61K 36/258; A61K 36/45; A61K 38/51; A61K 39/0008; A61K 47/24; A61K 47/52; A61K 8/37; A61K 8/466; A61K 8/498; A61K 8/673; A61K 8/678; A61K 8/68; A61K 8/735; A61K 8/92; A61K 8/9761; A61K 8/9794; A61K 9/0048; A61K 9/50; A61K 2039/5156; A61K 2039/5158; A61K 2039/55511; A61K 2039/55516; A61K 2039/572; A61K 31/045; A61K 31/12; A61K 31/122; A61K 31/132; A61K 31/137; A61K 31/197; A61K 31/205; A61K 31/352; A61K 31/415; A61K 31/422; A61K 31/7034; A61K 35/17; A61K 35/76; A61K 35/761; A61K 36/06; A61K 36/185; A61K 36/23; A61K 36/40; A61K 36/483; A61K 36/515; A61K 36/63; A61K 36/73; A61K 36/736; A61K 36/9066; A61K 38/05; A61K 39/00; A61K 39/001; A61K 39/0011; A61K 39/35; A61K 39/38; A61K 48/0058; A61K 8/0212; A61K 8/04; A61K 8/19; A61K 8/34; A61K 8/347; A61K 8/35; A61K 8/362; A61K 8/365; A61K 8/368; A61K 8/4926; A61K 8/494; A61K 8/4953; A61K 8/4986; A61K 8/671; A61K 8/736; A61K 8/86; A61K 8/9711; A61K 8/9717; A61K 8/9767; A61K 8/982; A61K 8/988; A61K 9/06; A61K 9/127; A61K 9/141; A61K 2039/57; A61K 2039/645; A61K 2236/00; A61K 2236/333; A61K 2800/31; A61K 2800/49; A61K 2800/75; A61K 2800/805; A61K 2800/874; A61K 31/18; A61K 31/196; A61K 31/23; A61K 31/381; A61K 31/404; A61K 31/407; A61K 31/4164; A61K 31/4168; A61K 31/425; A61K 31/426; A61K 31/427; A61K 31/4375; A61K 31/4412; A61K 31/4418; A61K 31/4422; A61K 31/4439; A61K 31/444; A61K 31/4545; A61K 31/4709; A61K 31/497; A61K 31/4985; A61K 31/5025; A61K 31/515; A61K 31/517; A61K 31/529; A61K 31/53; A61K 31/5386; A61K 31/55; A61K 31/5513; A61K 31/573; A61K 31/593; A61K 31/683; A61K 31/688; A61K 31/7004; A61K 31/7024; A61K 31/713; A61K 31/723; A61K 33/00; A61K 33/24; A61K 36/00; A61K 36/16; A61K 36/22; A61K 36/28; A61K 36/324; A61K 36/38; A61K 36/67; A61K 36/76; A61K 36/81; A61K 36/82; A61K 36/889; A61K 36/9068; A61K 38/12; A61K 38/1767; A61K 38/26; A61K 38/38; A61K 38/385; A61K 38/39; A61K 38/47; A61K 47/02; A61K 47/12; A61K 47/16; A61K 47/18; A61K 47/183; A61K 47/22; A61K 47/34; A61K 47/42; A61K 47/44; A61K 47/46; A61K 47/551; A61K 8/0229; A61K 8/062; A61K 8/064; A61K 8/14; A61K 8/23; A61K 8/24; A61K 8/26; A61K 8/342; A61K 8/42; A61K 8/447; A61K 8/46; A61K 8/732; A61K 8/891; A61K 8/922; A61K 8/9728; A61K 8/9771; A61K 9/006; A61K 9/0073; A61K 9/12; A61K 9/14; A61K 9/19; A61K 2800/52; A61K 47/06; A61K 47/36; A61K 8/39; A61K 2800/522; A61K 9/1277; A61K 31/07; A61K 31/715; A61K 8/355; A61K 8/67; A61K 8/97; A61Q 19/00; A61Q 19/08; A61Q 19/10; A61Q 15/00; A61Q 17/04; A61Q 19/007; A61Q 11/00; A61Q 19/02; A61Q 5/02; A61Q 19/008; A61Q 19/06; A61Q 19/005; A61Q 7/00; A61Q 9/04; A61Q 1/14; A61Q 19/001
See application file for complete search history.

(56) References Cited

FOREIGN PATENT DOCUMENTS

| | | | | |
|---|---|---|---|---|
| JP | H07-252114 A | 10/1995 | | |
| JP | H09-263513 A | 10/1997 | | |
| JP | H11-269096 A | 10/1999 | | |
| JP | 2000-178134 A | 6/2000 | | |
| JP | 2002-522570 A | 7/2002 | | |
| JP | 2002-348228 A | 12/2002 | | |
| JP | 2004-331629 A | 11/2004 | | |
| JP | 2004331629 | * 11/2004 | ............... | A61K 7/48 |
| JP | 2005-225865 A | 8/2005 | | |
| JP | 2005225865 | * 8/2005 | ............... | A61K 7/48 |
| JP | 2010-180206 A | 8/2010 | | |
| JP | 2013-095691 A | 5/2013 | | |
| JP | 2013095691 | * 5/2013 | ............... | A61K 8/67 |
| JP | 2013-199466 A | 10/2013 | | |
| JP | 2014-227386 A | 12/2014 | | |
| JP | 2019-026641 A | 2/2019 | | |
| WO | 0078283 A1 | 12/2000 | | |
| WO | 0219972 A2 | 3/2002 | | |
| WO | 2018003850 A1 | 4/2018 | | |

OTHER PUBLICATIONS

JP2013095691 translation, "Sakamoto". (Year: 2013).*
JP2005225865 translation (Year: 2005).*
International Preliminary Report on Patentability for International Application No. PCT/JP2018/048188 mailed Jul. 9, 2020.

(56) References Cited

OTHER PUBLICATIONS

Ahmad, I. et al., "Photostabilization of ascorbic acid with citric acid, tartaric acid and boric acid in cream formulations", International Journal of Cosmetic Science, 2012, vol. 34, No. 3, pp. 240-245, in particular, see abstract, table 2.
Midorikawa, Yusuke, "Effects of various additives on stability of ascorbic acid aqueous solution", Abstracts 4 of the 137th annual conference of the Pharmaceutical Society of Japan), Mar. 5, 2017, p. 128, No. 25PB-pm241, entire text, non-official translation.
International Search Report for International Application No. PCT/JP2018/048188 mailed Mar. 26, 2019.
Office Action issued Nov. 28, 2022 in corresponding Japanese Patent Application No. 2019-562174; 8 pages.
Office Action issued in CN application No. 201880083405.2; dated Dec. 28, 2022; 17 pages.
Office Action issued in CN application No. 201880083405.2; dated Jul. 21, 2023; 18 pages.
Decision of Rejection issued in CN application No. 201880083405.2; dated Mar. 23, 2024; 23 pages.

\* cited by examiner

EXTERNAL COMPOSITION CONTAINING ASCORBIC ACID AND/OR SALT THEREOF

This Application is a National Stage Entry of PCT/JP2018/048188, filed Dec. 27, 2018, which claims priority to Japanese Patent Application No. 2017-252208, filed Dec. 27, 2017, the applications of which are hereby incorporated by reference for all purposes as if fully set forth herein.

TECHNICAL FIELD

The present invention relates to an external composition containing an ascorbic acid and/or a salt thereof.

BACKGROUND ART

Ascorbic acids are known to exert various effects, such as anti-inflammatory, acne-reducing, whitening, anti-aging, and antioxidant effects, an effect of activating cells by promoting the synthesis of biological components such as collagen, and an effect of suppressing cell and DNA damage caused in epidermal keratinocytes by ultraviolet rays, and are widely used as a component of external preparations for skin in expectation of these effects.

Ascorbic acids are easily oxidized in the presence of water, for example, in aqueous solutions. Thus, there is a requirement to reduce the amount of water present in formulations containing an ascorbic acid. However, a reduced amount of water cannot lead to sufficient solubilization of the ascorbic acid.

For this reason, several methods have been investigated for stable solubilization of an ascorbic acid in aqueous external preparations for skin (for example, Patent Document 1: WO 02/19972; Patent Document 2: WO 00/78283; Patent Document 3: JP-A-2002-348228; and Patent Document 4: JP-A-2005-225865).

PRIOR ART DOCUMENTS

Patent Documents

Patent Document 1: WO 02/19972
Patent Document 2: WO 00/78283
Patent Document 3: JP-A-2002-348228
Patent Document 4: JP-A-2005-225865

SUMMARY OF THE INVENTION

Problems to be Solved by the Invention

The present invention aims at providing an external composition containing an ascorbic acid that has good properties.

Means for Solving the Problems

There are provided external compositions containing an ascorbic acid and/or a salt thereof, in which the ascorbic acid and/or salt thereof can be formulated at various concentrations.

Investigations by the present inventors have revealed that in cases where an ascorbic acid and/or a salt thereof is formulated at high concentrations into preparations, the ascorbic acid and/or salt thereof may not be dissolved during their production, and even when having been dissolved during their production, storage at low temperatures, such as at 4° C., leads to the precipitation of the ascorbic acid and/or salt thereof. Furthermore, it has been found that although there is no problem in quality, yellowing may occur especially in formulations in which a high concentration of ethoxydiglycol has been incorporated to improve use feeling.

On the basis of results from extensive studies to solve the above-mentioned problem, the present inventors have found that an external composition that is capable of suppression of the precipitation and decomposition of an ascorbic acid and is superior in the stability of and additionally in the transdermal absorbability (skin permeability) of the ascorbic acid is obtained by including (A) at least one selected from the group consisting of an ascorbic acid and an ascorbic salt, (B) a diol having 3 carbon atoms, (C) at least one selected from the group consisting of a low-molecular-weight betaine, an organic acid salt, an inorganic acid salt, a basic amino acid, a basic amino acid salt, 3-O-ethylascorbic acid, and a 3-O-ethylascorbic acid salt, and (D) water, and additionally setting the content of ethoxydiglycol to less than 30 mass %; thus, this has led to the completion of the present invention.

Accordingly, the present invention provides external compositions set forth in the embodiments below:

[Item 1]
An external composition, including
(A) at least one selected from the group consisting of an ascorbic acid and an ascorbic salt,
(B) a diol having 3 carbon atoms,
(C) at least one selected from the group consisting of a low-molecular-weight betaine, an organic acid salt, an inorganic acid salt, a basic amino acid, a basic amino acid salt, 3-O-ethylascorbic acid, and a 3-O-ethylascorbic acid salt, and
(D) water,
and a content of ethoxydiglycol of said composition is less than 30 mass %.

[Item 2]
The external composition according to Item 1, in which the component (B) is in an amount of 25 mass % or more of the external composition.

[Item 3]
The external composition according to Item 1 or 2, in which the component (D) is in an amount of 0.01 to 20 parts by mass relative to 1 part by mass of the total content of the component (A).

[Item 4]
The external composition according to any one of Items 1 to 3, in which the component (C) is at least one selected from the group consisting of trimethylglycine, carnitine, arginine, sodium citrate, sodium succinate, sodium pyrrolidonecarboxylate, 3-O-ethylascorbic acid, and a 3-O-ethylascorbic acid salt.

[Item 5]
The external composition according to any one of Items 1 to 4, in which the component (B) is 1,3-propanediol or propylene glycol.

[Item 6]
The external composition according to any one of Items 1 to 5, in which the ascorbic acid or salt thereof is in a concentration of 3 to 40 mass %.

[Item 7]
The external composition according to any one of Items 1 to 6, further including (E) a lower alcohol.

[Item 8]
The external composition according to any one of Items 1 to 7, in which the ethoxydiglycol is in an amount of 10 mass % or less of the external composition.

[Item 9]

The external composition according to any one of Items 1 to 8, in which the external composition is substantially free from ethoxydiglycol.

[Item 10]

The external composition according to any one of Items 1 to 9, in which the external composition is one that is a solubilized system having a transmittance of 85 to 100% at a wavelength of 700 nm.

[Item 11]

The external composition according to any one of Items 1 to 10, in which the external composition is for promoting the transdermal absorption of the ascorbic acid.

[Item 12]

A method of imparting stability to an external composition including (A) at least one selected from the group consisting of an ascorbic acid and an ascorbic salt, in which the method includes using in combination (A) at least one selected from the group consisting of ascorbic acid and an ascorbic salt, (B) a diol having 3 carbon atoms, (C) at least one selected from the group consisting of a low-molecular-weight betaine, an organic acid salt, an inorganic acid salt, a basic amino acid, a basic amino acid salt, 3-O-ethylascorbic acid, and a 3-O-ethylascorbic acid salt, and (D) water, and a content of ethoxydiglycol of said composition is less than 30 mass %.

Effect of the Invention

According to the present invention, it is possible to provide external compositions superior in stability.

MODE FOR CARRYING OUT THE INVENTION

In the specification, the unit "mass %" used to express the content of a given component in a composition is synonymous with "g/100 g" of the composition.

An external composition of the present invention is one including: (A) at least one selected from the group consisting of an ascorbic acid and an ascorbic salt, (B) a diol having 3 carbon atoms, (C) at least one selected from the group consisting of a low-molecular-weight betaine, an organic acid salt, an inorganic acid salt, a basic amino acid, a basic amino acid salt, 3-O-ethylascorbic acid, and a 3-O-ethylascorbic acid salt, and (D) water, and a content of ethoxydiglycol of said composition is less than 30 mass %.

The external composition of the present invention is stable and highly safe in a wide range of concentrations of (A) at least one selected from the group consisting of an ascorbic acid and an ascorbic salt.

[(A) at Least One Selected from the Group Consisting of an Ascorbic Acid and an Ascorbic Salt]

As an ascorbic acid used in the present invention, ones that are commercially available as a component of external preparations for skin in the field of pharmaceuticals, quasi drugs, or cosmetics can be used, which are usually of the L-form.

An ascorbic salt can also be used. Herein, the ascorbic salt is a pharmaceutically acceptable salt of an ascorbic acid. Examples of an ascorbic salt include, without limitation, for example, salts with organic bases (for example, salts with tertiary amines such as trimethylamine salts, triethylamine salts, monoethanolamine salts, triethanolamine salts, and pyridine salts, basic ammonium salts such as with arginine, and others), salts with inorganic bases (for example, ammonium salts, alkali metal salts such as sodium salts and potassium salts, alkaline earth metal salts such as calcium salts and magnesium salts, aluminum salts, and others). Particularly preferred ascorbic salts are sodium salts and potassium salts of ascorbic acids. Specific examples of an ascorbic salt include sodium ascorbate, sodium ascorbyl monophosphate, sodium ascorbyl diphosphate, sodium ascorbyl triphosphate, sodium ascorbyl-2-sulfate, and other.

In the present invention, the ascorbic acid or salts thereof as described above can be used alone or in combination of two or more.

In an external composition of the present invention, the total content of the component (A) relative to the total amount of the external composition is set as appropriate in relation to the other components. The total content of the component (A) is not particularly limited, and is preferably 0.1 mass % or more, more preferably 1 mass % or more, further preferably 2 mass % or more, further more preferably 3 mass % or more, and most preferably 10 mass % or more, relative to the total amount of the external composition. The total content of the component (A) is preferably 50 mass % or less, more preferably 40 mass % or less, further preferably 35 mass % or less, and further more preferably 30 mass % or less, relative to the total amount of the external composition. The total content of the component (A) is preferably 0.1 mass % to 50 mass %, more preferably 1 mass % to 40 mass %, further preferably 3 mass % to 40 mass %, further more preferably 3 mass % to 30 mass %, and most preferably 10 mass % to 30 mass %, relative to the total amount of the external composition.

[(B) Diols Having 3 Carbon Atoms]

A diol having 3 carbon atoms used in the present invention is not particularly limited, as long as the diol is employed as a component of external preparations for skin in the field of pharmaceuticals, quasi drugs, or cosmetics. The diol having 3 carbon atoms is, without limitation, preferably 1,3-propanediol (CAS No.: 504-63-2, designated as 1,3-Dihydroxypropane or Trimethylene Glycol in English) or propylene glycol (CAS No.: 57-55-6, designated as 1,2-Dihydroxypropane in English and as 1,2-propanediol alternatively in Japanese), with 1,3-propanediol being more preferable. For example, any one of 1,3-propanediol or propylene glycol can be used as the component (B). For these diols having 3 carbon atoms, commercially available products can be used as they are. From the viewpoint of alleviated skin irritation, improved feeling of use, and suppressed coloring, it is also a preferable embodiment to use 1,3-propanediol and propylene glycol in combination. It is more preferable that at least 1,3-propanediol is contained as the component (B) in the external composition.

In an external composition of the present invention, the total content of the component (B) is not particularly limited, and is preferably 20 mass % or more, more preferably 25 mass % or more, and further preferably 30 mass % or more, relative to the total amount of the external composition.

The total content of the component (B) is preferably 90 mass % or less, more preferably 85 mass % or less, and further preferably 80 mass % or less, relative to the total amount of the external composition.

The total content of the component (B) is preferably 20 to 90 mass %, more preferably 25 to 85 mass %, and further preferably 30 to 80 mass %, relative to the total amount of the external composition.

In the external composition of the present invention, the ratio of the formulation amount of the component (B) to that of the component (A) is not particularly limited, and is preferably 0.1 to 100 parts by mass, and more preferably 0.5 to 25 parts by mass, relative to 1 part by mass of the total content of the component (A).

[Component (C)]
(Low-Molecular-Weight Betaines)

As a low-molecular-weight betaine used in the present invention, compounds that are usually employed as a component of external preparations for skin in the field of pharmaceuticals, quasi drugs, or cosmetics can be used. In the present invention, the low-molecular-weight betaine refers to a compound with a molecular weight of 500 or less that forms a zwitterion within the molecule. Specific examples of such a compound include ones that have a quaternary ammonium salt group, a quaternary phosphonium salt group, a tertiary sulfonium salt group, or the like, and these hardly exhibit any properties as surfactants. Among them, preference is given to an N,N,N-trialkylamino acid represented by the following chemical formula:

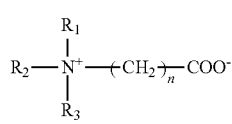

[Formula 1]

where $R_1$, $R_2$, and $R_3$ each independently represent an alkyl group having 1 to 6 carbon atoms, and n represents 1 to 6.

As $R_1$ to $R_3$, a wide range of linear or branched alkyl groups having 1 to 6 carbon atoms can be used. Accordingly, each of $R_1$ to $R_3$ is, by way of exemplification, a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group, an isohexyl group, a 3-methylpentyl group, a 2,2-dimethylbutyl group, a 2,3-dimethylbutyl group, or the like. $R_1$ to $R_3$ may be the same or different.

Specific examples of the N,N,N-trialkylamino acid are trimethylglycine, triethylglycine, tripropylglycine, and triisopropylglycine in the case of n=1, trimethyl-3-alanine in the case of n=2, trimethyl-γ-aminobutyric acid in the case of n=3, and so on, with trimethylglycine being preferable.

These low-molecular-weight betaines may be substituted, and specific examples of substituted betaines include N,N,N-trimethylalanine, N,N,N-triethylalanine, N,N,N-triisopropylalanine, N,N,N-trimethylmethylalanine, carnitine, acetylcarnitine, and others, with carnitine being preferable.

These can be synthesized. Alternatively, commercially available products can also be used as they are.

The low-molecular-weight betaines as described above can be used alone or in combination of two or more.

In an external composition of the present invention, the total content of a low-molecular-weight betaine(s) relative to the total amount of the external composition is set as appropriate in relation to the other components. The total content of a low-molecular-weight betaine(s) is preferably 0.00001 mass % or more, more preferably 0.0001 mass % or more, further preferably 0.001 mass % or more, more preferably 0.01 mass % or more, and most preferably 0.05 mass % or more, relative to the total amount of the external composition. The total content of a low-molecular-weight betaine(s) is preferably 30 mass % or less, more preferably 25 mass % or less, further preferably 20 mass % or less, more preferably 15 mass % or less, and most preferably 10 mass % or less, relative to the total amount of the external composition. The total content of a low-molecular-weight betaine(s) is preferably 0.00001 mass % to 30 mass %, more preferably 0.0001 mass % to 25 mass %, further preferably 0.001 mass % to 20 mass %, and most preferably 0.01 mass % to 10 mass %, relative to the total amount of the external composition.

In the external composition of the present invention, the ratio of the formulation amount of a low-molecular-weight betaine(s) to that of the component (A) is such that the total content of the low-molecular-weight betaine(s) is preferably 0.00005 to 1.0 part by mass, more preferably 0.0001 to 0.8 parts by mass, further preferably 0.0005 to 0.5 parts by mass, and most preferably 0.001 to 0.4 parts by mass, relative to 1 part by mass of the total content of the component (A).

(Organic Acid Salts)

As an organic acid salt used in the present invention, use can be made of compounds that are usually employed as a component of external preparations for skin in the field of pharmaceuticals, quasi drugs, or cosmetics.

The organic acid salt contributes to the stability of external compositions of the present invention.

In the present invention, an organic acid from which the organic acid salt is formed is an organic compound acid with an organic group and having a molecular weight of 1000 or less, preferably 700 or less, more preferably 500 or less, particularly preferably 300 or less. Organic acids are mostly carboxylic acids having a carboxyl group or groups, or sulfonic acids having a sulfo group or groups. More specifically, but without limitation, such organic acids include, for example, lactic acid, acetic acid, citric acid, tartaric acid, malic acid, succinic acid, oxalic acid, gluconic acid, fumaric acid, propionic acid, aspartic acid, pyrrolidone carboxylic acid, s-aminocaproic acid, glutamic acid, aminoethyl sulfonic acid, and others.

Herein, the salt forming an organic acid salt is a pharmaceutically acceptable one. Examples of an organic acid salt include, without limitation, for example, salts with organic bases (for example, salts with tertiary amines such as trimethylamine salts, triethylamine salts, monoethanolamine salts, triethanolamine salts, and pyridine salts, basic ammonium salts such as with arginine, and others), salts with inorganic bases (for example, ammonium salts, alkali metal salts such as sodium salts and potassium salts, alkaline earth metal salts such as calcium salts and magnesium salts, aluminum salts, and others). Particularly preferred organic acid salts are sodium salts and calcium salts of such organic acids as described above.

In the present invention, organic acid salts that are preferable include sodium lactate, sodium acetate, sodium citrate, sodium succinate, sodium oxalate, calcium gluconate, sodium pyrrolidonecarboxylate, and others.

These can be synthesized. Alternatively, commercially available products can also be used as they are.

The organic acid salts as described above can be used alone or in combination of two or more.

In an external composition of the present invention, the total content of an organic acid salt(s) relative to the total amount of the external composition is set as appropriate in relation to the other components. The total content of an organic acid salt(s) is preferably 0.0001 mass % or more, more preferably 0.001 mass % or more, further preferably 0.005 mass % or more, more preferably 0.01 mass % or more, and most preferably 0.05 mass % or more, relative to the total amount of the external composition. The total content of an organic acid salt(s) is preferably 10 mass % or less, more preferably 9 mass % or less, further preferably 8 mass % or less, more preferably 7 mass % or less, and most preferably 6 mass % or less, relative to the total amount of the external composition. The total content of an organic acid salt(s) is preferably 0.0001 mass % to 10 mass %, more preferably 0.001 mass % to 9 mass %, further preferably 0.005 mass % to 8 mass %, and most preferably 0.05 mass % to 6 mass %, relative to the total amount of the external composition.

In the external composition of the present invention, the ratio of the formulation amount of an organic acid salt(s) to that of the component (A) is such that the total content of the organic acid salt(s) is preferably 0.00003 to 0.8 parts by mass, more preferably 0.00005 to 0.7 parts by mass, further 0.00008 to 0.6 parts by mass, and most preferably 0.0001 to 0.5 parts by mass, relative to 1 part by mass of the total content of the component (A).

(Inorganic Acid Salts)

As an inorganic acid salt used in the present invention, use can be made of compounds that are usually employed as a component of external preparations for skin in the field of pharmaceuticals, quasi drugs, or cosmetics.

The inorganic acid salt contributes to the stability of external compositions of the present invention.

In the present invention, an inorganic acid includes, more specifically, but without limitation, nitric acid, phosphoric acid, sulfuric acid, sulfurous acid, boric acid, hydrofluoric acid, and others, by way of examples.

Herein, the salt forming an inorganic acid salt is a pharmaceutically acceptable one. Examples of an inorganic acid salt include, without limitation, for example, salts with inorganic bases (for example, alkali metal salts such as sodium salts and potassium salts, alkaline earth metal salts such as calcium salts and magnesium salts, aluminum salts, and others). Particularly preferred inorganic acid salts are sodium salts and calcium salts of such inorganic acids as described above.

In the present invention, inorganic acid salts that are preferable include sodium pyrosulfite, potassium pyrosulfite, sodium phosphate, potassium nitrate, sodium borate, and others. Among these, preference is given to sodium pyrosulfite.

These can be synthesized. Alternatively, commercially available products can also be used as they are.

The inorganic acid salts as described above may be used alone or in combination of two or more.

In an external composition of the present invention, the total content of a pyrosulfite(s) relative to the total amount of the external composition is set as appropriate in relation to the other components. The total content of a pyrosulfite(s) is preferably 0.00001 mass % or more, more preferably 0.0001 mass % or more, further preferably 0.0005 mass % or more, more preferably 0.001 mass % or more, and most preferably 0.005 mass % or more, relative to the total amount of the external composition. The total content of a pyrosulfite(s) is preferably 1 mass % or less, more preferably 0.8 mass % or less, further preferably 0.5 mass % or less, more preferably 0.4 mass % or less, and most preferably 0.3 mass % or less, relative to the total amount of the external composition. The total content of a pyrosulfite(s) is preferably 0.00001 mass % to 1 mass %, more preferably 0.0001 mass % to 0.8 mass %, further preferably 0.0005 mass % to 0.5 mass %, and most preferably 0.005 mass % to 0.3 mass %, relative to the total amount of the external composition.

In the external composition of the present invention, the ratio of the formulation amount of a pyrosulfite(s) to that of the component (A) is such that the total content of the pyrosulfite(s) is preferably-to-parts by mass, more preferably-to-parts by mass, further-to-parts by mass, and most preferably-to-parts by mass, relative to 1 part by mass of the total content of the component (A).

(Basic Amino Acids or Salts Thereof)

As a basic amino acid or salt thereof used in the present invention, compounds that are usually employed as a component of external preparations for skin in the field of pharmaceuticals, quasi drugs, or cosmetics can be used.

The basic amino acid or salt thereof contributes to the stability of external compositions of the present invention.

In the present invention, the basic amino acid refers to arginine, lysine, or histidine.

Herein, the basic amino acid salt is a pharmaceutically acceptable one. Examples of a basic amino acid salt include, without limitation, for example, salts with organic bases (for example, salts with tertiary amines such as trimethylamine salts, triethylamine salts, monoethanolamine salts, triethanolamine salts, and pyridine salts, basic ammonium salts such as with arginine, and others), salts with inorganic bases (for example, ammonium salts, alkali metal salts such as sodium salts and potassium salts, alkaline earth metal salts such as calcium salts and magnesium salts, aluminum salts, and others). Particularly preferred basic amino acid salts are sodium salts and calcium salts of such basic amino acids as described above.

In the present invention, a basic amino acid or salt thereof that is preferable includes arginine.

These can be synthesized. Alternatively, commercially available products can also be used as they are.

The basic amino acids or salts thereof as described above can be used alone or in combination of two or more.

In an external composition of the present invention, the total content of a basic amino acid(s) or salt(s) thereof relative to the total amount of the external composition is set as appropriate in relation to the other components. The total content of a basic amino acid(s) or salt(s) thereof is preferably 0.0001 mass % or more, more preferably 0.001 mass % or more, further preferably 0.005 mass % or more, more preferably 0.01 mass % or more, and most preferably 0.05 mass % or more, relative to the total amount of the external composition. The total content of a basic amino acid(s) or salt(s) thereof is preferably 10 mass % or less, more preferably 9 mass % or less, further preferably 8 mass % or less, more preferably 7 mass % or less, and most preferably 6 mass % or less, relative to the total amount of the external composition. The total content of a basic amino acid(s) or salt(s) thereof is preferably 0.0001 mass % to 10 mass %, more preferably 0.001 mass % to 9 mass %, further preferably 0.005 mass % to 8 mass %, and most preferably 0.05 mass % to 6 mass %, relative to the total amount of the external composition.

In the external composition of the present invention, the ratio of the formulation amount of a basic amino acid(s) or salt(s) thereof to that of the component (A) is such that the total content of the basic amino acid(s) or salt(s) is preferably 0.00003 to 0.8 parts by mass, more preferably 0.00005 to 0.7 parts by mass, further 0.00008 to 0.6 parts by mass, and most preferably 0.0001 to 0.5 parts by mass, relative to 1 part by mass of the total content of the component (A).

(3-O-Ethylascorbic Acid or Salts Thereof)

As 3-O-ethylascorbic acid or a salt thereof used in the present invention, use can be made of compounds that are usually employed as a component of external preparations for skin in the field of pharmaceuticals, quasi drugs, or cosmetics.

3-O-ethylascorbic acid can be synthesized by ethoxylating the hydroxyl group at the 3-position of ascorbic acid (by known methods described in, for example, JP-A-8-134055). For 3-O-ethylascorbic acid, commercially available products can also be used as they are. Commercially available products of 3-O-ethylascorbic acid include, by way of exemplification and not limitation, for example, not only "VC Ethyl", manufactured by Nippon Fine Chemical Co. Ltd., but also products manufactured by, for example, Junsei Chemical Co., Ltd.

The 3-O-ethylascorbic acid contributes to the stability of external compositions of the present invention.

These can be synthesized. Alternatively, commercially available products can also be used as they are.

The 3-O-ethylascorbic acid or salts thereof as described herein can be used alone or in combination of two or more.

3-O-ethylascorbic acid can also be used in the form of a salt thereof. Herein, the 3-O-ethylascorbic acid salt is a pharmaceutically acceptable one. Examples of a 3-O-ethylascorbic acid salt include, without limitation, for example, salts with organic bases (for example, salts with tertiary amines such as trimethylamine salts, triethylamine salts, monoethanolamine salts, triethanolamine salts, and pyridine salts, basic ammonium salts such as with arginine, and others), salts with inorganic bases (for example, ammonium salts, alkali metal salts such as sodium salts and potassium salts, alkaline earth metal salts such as calcium salts and magnesium salts, aluminum salts, and others). Particularly preferred 3-O-ethylascorbic acid salts are sodium salt and potassium salt of 3-O-ethylascorbic acid.

In an external composition of the present invention, the total content of 3-O-ethylascorbic acid or a salt(s) thereof relative to the total amount of the external composition is set as appropriate in relation to the other components. The total content of 3-O-ethylascorbic acid or a salt(s) thereof is preferably 0.0001 mass % or more, more preferably 0.001 mass % or more, further preferably 0.005 mass % or more, more preferably 0.01 mass % or more, and most preferably 0.02 mass % or more, relative to the total amount of the external composition. The total content of 3-O-ethylascorbic acid or a salt(s) thereof is preferably 10 mass % or less, more preferably 8 mass % or less, further preferably 6 mass % or less, more preferably 5 mass % or less, and most preferably 3 mass % or less, relative to the total amount of the external composition. The total content of 3-O-ethylascorbic acid or a salt(s) thereof is preferably 0.0001 mass % to 10 mass %, more preferably 0.001 mass % to 5 mass %, further preferably 0.005 mass % to 3 mass %, and most preferably 0.01 mass % to 3 mass %, relative to the total amount of the external composition.

In the external composition of the present invention, the ratio of the formulation amount of 3-O-ethylascorbic acid or a salt(s) thereof to that of component (A) is such that the total content of the 3-O-ethylascorbic acid or salt(s) thereof is preferably 0.00001 to 1 part by mass, more preferably 0.00005 to 0.8 parts by mass, further 0.0001 to 0.6 parts by mass, and most preferably 0.0002 to 0.5 parts by mass, relative to 1 part by mass of the total content of the component (A).

The component (C) can contribute to higher stability and transdermal absorbability of external compositions of the present invention.

With regard to the component (C), which is at least one selected from the group consisting of a low molecular weight betaine, an organic acid salt, an inorganic acid salt, a basic amino acid, a basic amino acid salt, 3-O-ethylascorbic acid, and a 3-O-ethylascorbic acid salt as described above, these members can be used alone, or in combination of any two or more.

Such combinations include, without limitation, trimethylglycine and a citrate, trimethylglycine and a succinate, trimethylglycine and pyrosulfurous acid or a salt thereof, 3-O-ethylascorbic acid or a salt thereof and a citrate, 3-O-ethylascorbic acid or a salt thereof and a succinate, 3-O-ethylascorbic acid or a salt thereof and trimethylglycine, 3-O-ethylascorbic acid or a salt thereof and carnitine, 3-O-ethylascorbic acid or a salt thereof and sodium pyrrolidonecarboxylate, 3-O-ethylascorbic acid or a salt thereof and pyrosulfurous acid or a salt thereof, and others.

In an external composition of the present invention, the total content of the component (C) is not particularly limited, and is preferably 0.005 mass % or more, and more preferably 0.01 mass % or more, relative to the total amount of the external composition. The total content of the component (C) is preferably 25 mass % or less, and more preferably 15 mass % or less, relative to the total amount of the external composition. The content of the component (C) is preferably 0.005 mass % to 25 mass %, and more preferably 0.01 mass % to 15 mass %, relative to the total amount of the external composition.

In the external composition of the present invention, the ratio of the formulation amount of the component (C) to that of the component (A) is preferably 0.00001 to 3 parts by mass, more preferably 0.0005 to 2 parts by mass, further preferably 0.0001 to 1 part by mass, even more preferably 0.005 to 0.9 parts by mass, and most preferably 0.008 to 0.8 parts by mass, relative to 1 part by mass of the total content of the component (A).

[(D) Water]

An external composition of the present invention is a liquid composition including water. The percentage of water in the external composition is, without limitation, preferably 0.01 mass % to 60 mass %, more preferably 0.01 mass % to 50 mass %, and particularly preferably 0.1 mass % to 40 mass %, relative to the external composition.

In the external composition of the present invention, the ratio of the formulation amount of the component (D) to that of the component (A) is not particularly limited, and is preferably 0.01 to 10 parts by mass, more preferably 0.1 to 5 parts by mass, and most preferably 0.2 to 3 parts by mass, relative to 1 part by mass of the total content of the component (A).

Thus, an embodiment of the present invention makes it possible that the precipitation of the ascorbic acid or salt thereof is suppressed even in compositions containing a small amount of water. In this embodiment, it further becomes possible to suppress the decomposition of the ascorbic acid.

[Ethoxydiglycol (Diethylene Glycol Monoethyl Ether)]

In the present invention, an external composition of the present invention does not contain ethoxydiglycol or otherwise contain the ethoxydiglycol in an amount of less than 30 mass %, mainly from the viewpoint of improving the stability of the compositions. The ethoxydiglycol contained in an amount of less than 30 mass % in the external composition is not particularly limited, as long as the ethoxydiglycol is employed as a component of external preparations for skin in the field of pharmaceuticals, quasi drugs, or cosmetics.

In an external composition of the present invention, the content of ethoxydiglycol is less than 30 mass %, relative to the total amount of the external composition. Preferably, the content of ethoxydiglycol is 10 mass % or less, relative to the total amount of the external composition. More preferably, the content of ethoxydiglycol is 5 mass % or less, relative to the total amount of the external composition. In some cases, no ethoxydiglycol may be contained in the external compositions.

The total content of ethoxydiglycol is 0 or more and less than 30 mass %, more preferably 0 to 10 mass %, and further preferably in the order of 0 to 5 mass %.

In the external composition of the present invention, the ratio of the formulation amount of ethoxydiglycol component to that of the component (A) is preferably 0 to 10 parts by mass, and more preferably 0 to 5 parts by mass, relative to 1 part by mass of the total content of the component (A). In some cases, the ratio of the formulation amount of ethoxydiglycol to that of the component (A) can be 0.001 to 10 parts by mass, or 0.01 to 5 parts by mass, relative to 1 part by mass of the total content of the component (A).

An external composition of the present invention is one that has good stability by containing the above-described components (A), (B), (C), and (D), and specifying the content of the ethoxydiglycol.

[Glycol Ethers]

In the present invention, it is preferable that an external composition of the present invention does not contain a glycol ether other than ethoxydiglycol or otherwise contain the glycol ether together with ethoxydiglycol in a total amount of less than 40 mass %, mainly from the viewpoint of improving the stability of the compositions. The glycol ether other than ethoxydiglycol is not particularly limited, as long as the glycol ether is employed as a component of external preparations for skin in the field of pharmaceuticals, quasi drugs, or cosmetics. The glycol ether can be one that dissolves in an amount of 10 g or more with respect to 100 g of water. Examples of such a glycol ether include, by way of example, ones with a degree of polymerization of 2 or less. Specifically, these can be, by way of example, diethylene glycol monomethyl ether, diethylene glycol monopropyl ether, diethylene glycol monobutyl ether, diethylene glycol monoisobutyl ether, diethylene glycol dimethyl ether, ethylene glycol monobutyl ether, ethylene glycol monomethyl ether, ethylene glycol monoethyl ether, triethylene glycol monobutyl ether, tetraethylene glycol monobutyl ether, propylene glycol monomethyl ether, propylene glycol monoethyl ether, propylene glycol monopropyl ether, dipropylene glycol monomethyl ether, dipropylene glycol monoethyl ether, dipropylene glycol monopropyl ether, etc. Furthermore, typical examples of such glycol ethers are diethylene glycol monomethyl ether, diethylene glycol monopropyl ether, diethylene glycol monobutyl ether, diethylene glycol monoisobutyl ether, diethylene glycol dimethyl ether, ethylene glycol monobutyl ether, ethylene glycol monomethyl ether, ethylene glycol monoethyl ether, triethylene glycol monobutyl ether, tetraethylene glycol monobutyl ether, propylene glycol monomethyl ether, propylene glycol monoethyl ether, propylene glycol monopropyl ether, dipropylene glycol monomethyl ether, dipropylene glycol monoethyl ether, and dipropylene glycol monopropyl ether. Especially, typical examples of such glycol ethers are diethylene glycol monomethyl ether, diethylene glycol monopropyl ether, ethylene glycol monobutyl ether, triethylene glycol monobutyl ether, tetraethylene glycol monobutyl ether, propylene glycol monomethyl ether, propylene glycol monoethyl ether, propylene glycol monopropyl ether, dipropylene glycol monomethyl ether, dipropylene glycol monoethyl ether, and dipropylene glycol monopropyl ether.

These glycol ethers can be used alone or in combination of two or more.

In an external composition of the present invention, the total content of a glycol ether(s) together with ethoxydiglycol is preferably less than 40 mass %, further preferably less than 30 mass %, and more preferably 10 mass % or less, relative to the total amount of the external composition. Alternatively, no glycol ether may be contained in the external composition.

The total content of a glycol ether(s) together with ethoxydiglycol is preferably 0 or more and less than 40 mass %, more preferably 0 or more and less than 30 mass %, further preferably in the order of 0 to 10 mass %, and most preferably in the order of 0 to 5 mass %.

In the external composition of the present invention, the ratio of the formulation amount of the glycol ether component to that of the component (A) is preferably 0 to 20 parts by mass, and more preferably 0 to 10 parts by mass, relative to 1 part by mass of the total content of the component (A). In some cases, the ratio of the formulation amount of the glycol ether component to that of the component (A) can be 0.001 to 20 parts by mass, or 0.01 to 10 parts by mass, relative to 1 part by mass of the total content of the component (A).

An external composition of the present invention can also be one that has good stability by containing the above-described components (A), (B), (C), and (D), and specifying the content of all the glycol ethers.

[(E) Lower Alcohols]

In addition to the above-described components (A), (B), (C), and (D), and if present, the glycol ether(s) such as ethoxydiglycol, an external composition of the present invention may include (E) a lower alcohol, from the viewpoint of improving the use feeling and promoting the stability and transdermal absorption of the compositions, unless the lower alcohol does not impair the effects of the present invention.

A lower alcohol used in the present invention is not particularly limited, as long as the lower alcohol is employed as a component of external preparations for skin in the field of pharmaceuticals, quasi drugs, or cosmetics. As used herein, a "lower alcohol" refers to a $C_1$-$C_6$ alcohol. Among these alcohols, especially a $C_1$-$C_3$ alcohol can be preferably used. Examples of such an alcohol include methanol, ethanol, n-propanol, isopropanol, and the like.

In an external composition of the present invention, when containing a component (E), the total content of the component (E) is preferably 0.1 mass % or more, and more preferably 0.5 mass % or more, relative to the total amount of the external composition.

The total content of the component (E) is preferably 25 mass % or less, and more preferably 20 mass % or less, relative to the total amount of the external composition.

The total content of the component (E) is preferably 0.001 to 25 mass %, more preferably 0.1 to 25 mass %, and further preferably 0.5 to 20 mass %, relative to the total amount of the external composition.

In the external composition of the present invention, the ratio of the formulation amount of the component (E) to that of the component (A) is preferably 0.001 to 8 parts by mass, and more preferably 0.005 to 5 parts by mass, relative to 1 part by mass of the total content of the component (A).

[Polyhydric Alcohols]

In addition to the above-described components (A), (B), (C), and (D), and when contained, the ethoxydiglycol in less than a specified amount, an external composition of the present invention may include a polyhydric alcohol, unless the polyhydric alcohol does not impair the effects of the present invention.

A polyhydric alcohol used in the present invention is not particularly limited, as long as the polyhydric alcohol is employed as a component of external preparations for skin in the field of pharmaceuticals, quasi drugs, or cosmetics.

The polyhydric alcohol may be added for moisture retention or as a solubilizing agent, without limitation to these purposes. Specific examples of the polyhydric alcohol are glycerin, diglycerin, dipropylene glycol, 1,3-butylene glycol, 3-methyl-1,3-butanediol, and the like. Preference is given to 1,3-butylene glycol and dipropylene glycol.

When a polyhydric alcohol is contained in the external composition, the total content of the polyhydric alcohol together with the component (B) is preferably 10 to 90 mass %, more preferably 20 to 80 mass %, further preferably 25 to 85 mass %, and particularly preferably in the order of 30 to 70 mass %.

[Other Components]

It is possible that in addition to the above-described components (A), (B), (C), and (D), and when contained, ethoxydiglycol in less than a specified amount, one or a combination of two or more of various components are further formulated in external compositions of the present invention, for example, whitening ingredients, anti-inflammatory ingredients, antibacterial ingredients, cell activating ingredients, astringent ingredients, antioxidant ingredients, acne-reducing ingredients, anti-aging ingredients, ingredients for promoting the synthesis of biological components such as collagen, blood circulation promoting ingredients, moisturizing ingredients, anti-aging ingredients, and others, in order to enhance or augment effects of ascorbic acid or to add other useful effects. It is preferable that one or more of a whitening ingredient, an anti-inflammatory ingredient, an antibacterial ingredient, a cell activating ingredient, an astringent ingredient, an antioxidant ingredient, an anti-aging ingredient, or a moisturizing ingredient are formulated in the external composition. Particularly preferable as a combination of these ingredients are combinations with a whitening ingredient, combinations of a whitening ingredient and an antioxidant ingredient, combinations with an antioxidant ingredient, combinations with an anti-aging ingredient, and combinations of a whitening ingredient and an anti-aging ingredient. The respective ingredients are not particularly limited and can be selected and used as appropriate, as long as they each have been used or will be used as a component of external preparations for skin in the field of pharmaceuticals, quasi drugs, or cosmetics.

It is also possible that in addition to the above-described ingredients, an external composition of the present invention further has a surfactant, a solubilizing agent, an oil or fat, a sugar, or a transdermal absorption promoter formulated therein. In particular, formulation of a surfactant, a solubilizing agent, or an oil or fat can lead to more improvement in the stability in aqueous solvents of the ascorbic acid, and the effectiveness and use feeling of the external composition.

In external compositions of the present invention, various ingredients that are commonly used as a component of external preparations for skin in the field of pharmaceuticals, quasi drugs, or cosmetics can be formulated as necessary, for example, amino acids, irritation reducing agents, thickeners, preservatives, UV protectants, colorants, dispersants, additional pH adjusters, perfumes, and others, within a quantitative and qualitative range that does not impair the properties of the composition, such as appearance stability and viscosity, and the effects of the present invention. These ingredients can be optionally used alone or in combination of two or more.

External compositions of the present invention, which include (A) at least one selected from the group consisting of an ascorbic acid and an ascorbic salt, (B) a diol having 3 carbon atoms, (C) at least one selected from the group consisting of a low molecular weight betaine, an organic acid salt, an inorganic acid salt, a basic amino acid, a salt of a basic amino acid, 3-O-ethylascorbic acid, and a 3-O-ethylascorbic acid salt, and (D) water, and have ethoxydiglycol in amount of less than 30 mass %, can be prepared into a variety of desired forms of products, such as pastes, mousses, gels, liquids, emulsions, creams, sheets (supported on substrates), aerosols, and sprays, by formulating and mixing the above-described optional ingredients thereinto as necessary, and further formulating other solvents, bases usually used in external preparations, and the like thereinto as necessary. These products can be produced by usual methods used in the art.

It is particularly preferable that external compositions of the present invention are transparent or translucent compositions having an ascorbic acid and/or a salt thereof solubilized therein. Here, "solubilized" is defined as follows. For example, when UV-visible spectrophotometry is done using a spectrophotometer or photoelectric photometer UV-2450 (manufactured by Shimadzu Corporation), the transmittance of the composition at a wavelength of 700 nm is in the range of 80 to 100%, preferably 85 to 100%, and more preferably 90 to 100%, with the proviso that the transmittance of water is set to be 100%. Compositions of the present invention in which an ascorbic acid and/or a salt thereof is solubilized are transparent or translucent in appearance. More specifically, the method by which the transmittancy of external compositions is measured is in accordance with the one described in The Japanese Pharmacopoeia Sixteenth Edition, [B] General Tests, 2. Physical Methods, Spectroscopic Method, 2.24 Ultraviolet-visible spectrophotometry.

[Viscosity]

External compositions of the present invention can be prepared as a composition with an appropriate viscosity that is desirable in using the composition as an external composition employed particularly for application to the skin. The viscosity of the external compositions of the present invention is not particularly limited. For example, the external composition has a viscosity of usually about 300 mPa·s or less, preferably about 200 mPa·s or less, more preferably about 100 mPa·s or less, and most preferably about 50 mPa·s or less, as measured at 25° C. using an E-type viscometer. More specifically, the method by which the viscosity of external compositions is measured is in accordance with the one described in The Japanese Pharmacopoeia Sixteenth Edition, [B] General Tests, 2. Physical Methods, Other Physical Methods, 2.53 Viscosity Determination, 2. Method 2 Viscosity measurement by rotational viscometer, 2.1.3 Core-flat plate-type rotational viscometer (cone plate type viscometer).

[pH]

An external composition of the present invention only needs to be of liquid that usually has a pH of 1 to 8. Desirably, the external composition has a pH in an acidic range of preferably pH 2-7, more preferably pH 2-6, and further more preferably pH 2-4.5, in terms of stability of the ascorbic acid, low degree of irritation to skin and mucous membranes, and good feeling of use on the skin.

[Use]

An external composition of the present invention are especially effective as whitening agents, anti-inflammatory agents, and anti-aging agents, and have effects, for example, of prevention or treatment of acne, and of anti-oxidation. Further, when applied to the skin, the composition may lead to an enhanced feeling of skin transparency, the moisture being retained, and the texture of the skin being improved, thereby providing the effect of reducing the roughness of the skin. In addition, the composition not only may make pores less noticeable and provide effects, for example, of caring and moisturizing the skin, but also can be used for prevention or treatment of freckles.

External compositions of the invention can be formed into ones that are used in field of cosmetics, topical medicines, or topical quasi-drugs, for example, basic cosmetics such as serums, face lotions, sunscreen creams, emulsions, creams, lotions, oils, and packs; makeup cosmetics such as foundations, lipsticks, lip creams, mascaras, eye shadows, eyeliners, eyebrow pencils, and nail polishers; cleaning preparations such as facial cleansers or cleansing agents, and body cleansers; and axillary odor inhibitors, athlete's foot treating agents, antipruritic preparations, wound healing agents, wiping agents, cleaning agents, anti-inflammatory analgesics, acne treating agents, hemorrhoidal agents, disinfectants, whitening agents, and UV protection agents. From the viewpoint of the effect of acting on the skin, the present invention is preferably used in products to be applied to the outer skin, such as external preparations for skin (preparations for application to the outer skin).

[Stabilization Methods]

The present invention also includes a method for stabilizing (A) at least one selected from the group consisting of an ascorbic acid and an ascorbic salt. In the present invention, according to the method for stabilizing an ascorbic acid, a preparation that is stable while containing an ascorbic acid or a salt thereof can be formed by using, in combination, (A) at least one selected from the group consisting of an ascorbic acid and an ascorbic salt, (B) a diol having 3 carbon atoms, (C) at least one selected from the group consisting of a low-molecular-weight betaine, an organic acid salt, an inorganic acid salt, a basic amino acid, a basic amino acid salt, 3-O-ethylascorbic acid, and a 3-O-ethylascorbic acid salt, and (D) water, and setting the content of ethoxydiglycol to less than 30 mass %. In particular, a preparation can be formed that is stable while containing an ascorbic acid or a salt thereof in a high concentration (for example, 15 mass % or more, 20 mass % or more, or the like). Therefore, the present invention relates to a method of imparting stability to an external composition including (A) at least one selected from the group consisting of an ascorbic acid and an ascorbic salt, in which the method includes using in combination (A) at least one selected from the group consisting of an ascorbic acid and an ascorbic salt, (B) a diol having 3 carbon atoms, (C) at least one selected from the group consisting of a low-molecular-weight betaine, an organic acid salt, an inorganic acid salt, a basic amino acid, a basic amino acid salt, 3-O-ethylascorbic acid, and a 3-O-ethylascorbic acid salt, and (D) water, and setting the content of ethoxydiglycol to less than 30 mass %. Here, "stabilizing" means that the stability of an ascorbic acid and an ascorbic salt is ensured, without limitation, for example, under high or low temperature conditions. Specifically, by "stabilizing" is meant that also in cases where the external composition is stored at least for 1 week at 4° C., the precipitation of the ascorbic acid or salt thereof is inhibited, or alternatively that changes in its appearance, such as coloring, is suppressed also after storage at 50° C. or after storage at 40° C.

In the method of the present invention, using in combination (A) at least one selected from the group consisting of an ascorbic acid and an ascorbic salt, (B) a diol having 3 carbon atoms, (C) at least one selected from the group consisting of a low-molecular-weight betaine, an organic acid salt, an inorganic acid salt, a basic amino acid, a basic amino acid salt, 3-O-ethylascorbic acid, and a 3-O-ethylascorbic acid salt, and (D) water, and setting the content of ethoxydiglycol to less than 30 mass %, as well as their contents, are the same as for the above-described external compositions. Furthermore, a product obtained by the method can be used according to known or conventional usage and dosage, from once to several times per day, depending on the intended use, etc.

[Improvement in Use Feeling]

The present invention also makes it possible to improve the use feeling of an external composition including (A) at least one selected from the group consisting of an ascorbic acid and an ascorbic salt. In the present invention, the external composition can be provided with a good feeling of use, while containing an ascorbic acid or a salt thereof, by using in combination (A) at least one selected from the group consisting of an ascorbic acid and an ascorbic salt, (B) a diol having 3 carbon atoms, (C) at least one selected from the group consisting of a low-molecular-weight betaine, an organic acid salt, an inorganic acid salt, a basic amino acid, a basic amino acid salt, 3-O-ethylascorbic acid, and a 3-O-ethylascorbic acid salt, and (D) water, and setting the content of ethoxydiglycol to less than 30 mass %. In particular, a good feeling of use can be achieved while containing an ascorbic acid or a salt thereof in a high concentration (e.g., 10 mass % or more, 20 mass % or more, or the like).

In order that in the present invention, the external composition is provided with a good feeling of use, using in combination (A) at least one selected from the group consisting of an ascorbic acid and an ascorbic salt, (B) a diol having 3 carbon atoms, (C) at least one selected from the group consisting of a low-molecular-weight betaine, an organic acid salt, an inorganic acid salt, a basic amino acid, a basic amino acid salt, 3-O-ethylascorbic acid, and a 3-O-ethylascorbic acid salt, and (D) water, and setting the content of ethoxydiglycol to less than 30 mass %, as well as their contents, are the same as for the above-described external compositions. Here, the good feeling of use refers to at least one or all of permeation feeling, low stickiness, reduced irritation, or smooth skin, when the external composition is applied to the skin.

EXAMPLES

Now, the present invention will be specifically described with reference to examples, but is not limited to the examples which follow. The amounts of the respective components in the tables described below are given in units of mass %.

External compositions having the compositions listed in the tables below were prepared according to usual methods. Unless otherwise specified, the numerical values for the components in the tables are expressed in mass %.

[Test 1 for Confirmation of Ascorbic Acid Precipitation Suppression]

A visual examination was made of the presence or absence of ascorbic acid precipitation when external compositions according to some Examples and Comparative Examples of the invention were stored in preparations at a low temperature. Specifically, according to each of the formulae (in mass %) described in the tables below of various formulations, a composition was prepared by adding ascorbic acid to a mixed solution of the various components, heating and mixing the mixture at 60° C. for 10 minutes to dissolve the ascorbic acid. The composition prepared was filled into transparent glass bottles, which were then left to stand at 4° C. under light-shielding conditions and stored for 1 week or for 4 weeks. The respective test solutions were subjected to visual examination to determine the presence or absence of precipitated crystals.

<Criteria for Evaluation>

○: Conditions in which precipitates cannot be visually confirmed.

x: Conditions in which precipitates can be visually confirmed.

[Test 2 for Confirmation of Ascorbic Acid Precipitation Suppression]

In order to evaluate particularly the stability of ascorbic acid contained at high concentrations, a visual examination was made of the presence or absence of ascorbic acid precipitation when external compositions according to some Examples and Comparative Examples of the invention were stored under severe conditions at a temperature below freezing point. Specifically, according to each of the formulae (in mass %) described in the tables below of various formulations, a composition was prepared by adding ascorbic acid to a mixed solution of the various components, heating and mixing the mixture at 60° C. for 10 minutes to dissolve the ascorbic acid. The composition prepared was filled into transparent glass bottles, which were then left to stand at −8° C. under light-shielding conditions and stored for 1 week. The respective test solutions were subjected to visual examination to determine the presence or absence of precipitated crystals.

<Criteria for Evaluation>

○: Conditions in which precipitates cannot be visually confirmed.

x: Conditions in which precipitates can be visually confirmed.

[Test for Confirmation of Coloring Suppression]

A visual examination was made of the presence or absence of the coloring of external compositions with a color difference meter according to some Examples and Comparative Examples of the invention after storage at 40° C. to 50° C. Specifically, according to each of the formulae (in mass %) described in the tables below of various formulations, an external composition was prepared by adding ascorbic acid to a mixed solution of the components, heating and mixing the mixture at 60° C. for 10 minutes to dissolve the ascorbic acid. The external composition prepared was filled into transparent glass bottles, which were then left to stand in a thermo-hygrostat at 40° C. or 50° C. for a period of 1 week to 4 weeks. The container was taken out of the thermostat at the time of each measurement, equilibrated at 25° C., and subjected to evaluation of the coloring of the composition. The presence or absence and the degree of coloring were determined for the respective test solutions by visual observation and with a color difference meter.

<Criteria for Evaluation>

○: a state with no or a little coloring change

Δ: a state with coloring change, although not remarkable x: a state with remarkable coloring change The measurements with a color difference meter were made as follows. One milliliter of a test solution was put into a glass cell (CM-A97, having a thickness of 2 mm), and the color difference was measured with a spectrophotometer CM-5 (manufactured by KONICA MINOLTA INC.) to determine the b-value. As the measurement value, the value Δb* was used, which is a difference between the color difference for the composition and that for purified water used as a blank. The change in color difference was calculated by the following formula:

(Amount of change in color difference (Δ$b$ value))= (measured value of test liquid after heated storage ($b$-value after accelerated test))−(measured value of test liquid before heated storage ($b$-value before accelerated test))

The b-value is used as an indicator of transparency. Therefore, the smaller the Δb value, the less the degree of coloring.

The Δb* ratio represents a ratio of the Δb values for Examples and Comparative Examples when the value of color difference for a specified external composition in the tables was used as a reference (1).

[Test for Transdermal Absorbability of Ascorbic Acid]

An examination was made of the transdermal absorbability of external compositions according to some Examples and Comparative Examples of the present invention. External compositions with improved transdermal absorbability lead to the penetration of the ascorbic acid into the inside of the skin, and thus are expected to have a higher anti-aging effect as a composition. Therefore, in some cases, it becomes possible to exert the effect of the ascorbic acid deep into the inside of the stratum corneum.

The transdermal absorbability of ascorbic acid for external compositions prepared in Examples and Comparative Examples was confirmed by determining the amount of the ascorbic acid penetrated into the stratum corneum using an evaluation by means of stratum corneum stripping.

Specifically, first, the amount of the ascorbic acid in the stratum corneum that was a component having penetrated into the skin of an upper arm and forearm of a healthy human was determined by tape stripping. The determination was done using, as subjects, a number of healthy persons who had given voluntary consent to participate in this study. A piece of cotton into which 750 μL of an external composition according to Examples or Comparative Examples had been impregnated was attached to an inner area (1.5 cm×1.5 cm) of the upper arm of the subject, and left to stand for 5 minutes. After removing the cotton, the composition sample remaining on the surface of the skin was removed with a new piece of cotton, and the skin was kept as it is for 30 minutes. This time period was taken to be a sample penetration time. After that, a mending tape (manufactured by SUMITOMO 3M LIMITED) was used to carry out seven rounds in succession of tape stripping at the applied site, thereby to exfoliate keratinocytes. All or the fourth to seventh strips of the tape strips obtained were used as samples for measurement. The number of tape stripping was determined using a preliminary test to confirm that a required amount of keratinocytes was peeled off for each round of tape stripping and there was no development of inflammation or pain after the tape stripping.

The samples for measurement thus obtained were subjected to extraction with 1 mL of an extraction solvent of a mixture of Tritonx-100 (manufactured by MP Biomedicals), mercaptoethanol (manufactured by Wako Pure Chemical Industries, Ltd.), and purified water (1:1:1000). The amount (μg/mL) of permeation of ascorbic acid was determined by HPLC from an extracted solution from which foreign materials had been removed with a 0.45 μm syringe filter (manufactured by GL Science). The determination was made by submitting the resulting extracted solution to an Agilent HPLC system equipped with a reversed-phase column (CAPCELL PAK C18 SG120, manufactured by Shiseido Company, Limited) (using a mobile phase of acetonitrile/0.02 M phosphoric acid solution (pH 3.0) (1:9) and an absorbance detection wavelength of 270 nm) and measuring the amount of L-ascorbic acid contained in the solution. A comparison of the results was performed by using, as an amount of penetration of ascorbic acid (μg/cm$^2$), the averaged value of the measured values from the measurement samples collected from three areas on the arm of one subject.

The detection of ascorbic acid by HPLC was performed with a reverse phase column (CAPCELL PAK C18 SG120, manufactured by Shiseido Company, Limited) using an ultraviolet absorption photometer at a wavelength of 270 nm, and the content of ascorbic acid in the extracted solution was calculated using a calibration curve.

[Test for Use Feeling of External Compositions Containing Ascorbic Acid]

A test for use feeling of external compositions according to Examples and Comparative Examples was performed on three healthy subjects by applying an appropriate amount (about 20 mg) of the external composition to an arm (inner forearm) of the subject. In the test, the respective external compositions were evaluated for each of the following: a feeling of permeation, the presence or absence of stickiness, the presence or absence of irritation, and the smoothness of the skin, by placing them at room temperature, at which they are usually used, and making the subjects unaware of which composition was used.

Evaluation results were scored as follows, such that for the respective evaluation items, the average values for the three subjects were obtained.

5: high penetration; not sticky; not irritative; and smooth
4: slight penetration; not so sticky; not so irritative; and slightly smooth
3: neither; neither; neither; and neither
2: little penetration; slightly sticky; slightly irritative; and not so smooth
1: almost no penetration; sticky; irritative; and not smooth Examples 1 to 12 and Comparative Examples 1 to 6

Tables 1 and 2 below show the results of the test 1 for confirmation of ascorbic acid precipitation suppression and the test for transdermal absorbability of ascorbic acid for compositions of Examples and Comparative Examples. The N number indicates the number of subjects.

The numerical values described in the row describing the result of the transdermal absorbability test for Examples 1 to 3 are values obtained as ratios relative to the amount of transdermal absorption of ascorbic acid for Comparative Example 2, which was set to be 1.

Ratio=(transdermal absorption amount for the composition of any of Examples (μg/cm$^2$)/(transdermal absorption amount for the composition of Comparative Example 2 (μg/cm$^2$)

Furthermore, regarding these ratios, the numerical values described in the row describing the transdermal absorption for Comparative Examples 1, 3, and 4 are values obtained as ratios relative to the amount of transdermal absorption of ascorbic acid for the composition of Comparative Example 2, which was set to be 1, as indicated below.

Ratio=(transdermal absorption amount for the composition of any of Comparative Example, 3, or 4 (μg/cm$^2$)/(transdermal absorption amount of the composition of Comparative Example 2(μg/cm$^2$)

TABLE 1

| Component name | Example 1 | Example 2 | Example 3 |
|---|---|---|---|
| Ascorbic acid | 15 | 15 | 15 |
| Propylene glycol | 60 | 40 | 60 |
| Trimethylglycine | 1.5 | 1.5 | 1.5 |
| Purified water | 18.5 | 38.5 | 23.5 |
| Anhydrous ethanol | 5 | 5 | — |
| Total | 100 | 100 | 100 |
| Ascorbic acid precipitation after 1 week at 4° C. | ○ | ○ | ○ |
| Ascorbic acid precipitation after 4 weeks at 4° C. | ○ | ○ | ○ |
| Transdermal absorbability test (4th to 7th tape strips) (ratio) N = 4 | 4.34 | 3.37 | 3.23 |

TABLE 2

| Component name | Comparative Example 1 | Comparative Example 2 | Comparative Example 3 | Comparative Example 4 |
|---|---|---|---|---|
| Ascorbic acid | 15 | 15 | 15 | 15 |
| Propylene glycol | 60 | — | — | — |
| Trimethylglycine | — | 1.5 | 1.5 | 1.5 |
| Purified water | 20 | 18.5 | 18.5 | 18.5 |
| 1,3-Butylene glycol | — | 60 | — | — |
| Dipropylene glycol | — | — | 60 | — |
| Anhydrous ethanol | 5 | 5 | 5 | 65 |
| Total | 100 | 100 | 100 | 100 |
| Ascorbic acid precipitation after 1 week at 4° C. | x | x | ○ | x |
| Ascorbic acid precipitation after 4 weeks at 4° C. | x | x | x | x |
| Transdermal absorbability test (4th to 7th tape strips) (ratio) N = 4 | 2.37 | 1 | 1.13 | 1.99 |

It has been confirmed that the compositions of these Examples suppressed the precipitation of ascorbic acid also during storage at low temperature. Surprisingly, the compositions of these Examples have been further found to be superior also in transdermal absorbability.

Table 3 shows the results of the test 1 for confirmation of ascorbic acid precipitation suppression.

TABLE 3

| Component name | Example 4 | Example 5 | Example 6 | Example 7 | Example 8 |
|---|---|---|---|---|---|
| Ascorbic acid | 15 | 15 | 15 | 15 | 15 |
| Propylene glycol | 40 | 40 | 30 | — | — |
| 1,3-Propanediol | — | — | — | 30 | 25 |
| Trimethylglycine | 1.5 | 1.5 | 1.5 | 1.5 | 1.5 |
| Purified water | 18.5 | 18.5 | 18.5 | 18.5 | 18.5 |
| 1,3-Butylene glycol | — | 20 | — | 30 | — |
| Dipropylene glycol | 20 | — | 30 | — | 35 |
| Anhydrous ethanol | 5 | 5 | 5 | 5 | 5 |
| Total | 100 | 100 | 100 | 100 | 100 |
| Ascorbic acid precipitation after 1 week at 4° C. | ○ | ○ | ○ | ○ | ○ |

TABLE 3-continued

| Component name | Example 4 | Example 5 | Example 6 | Example 7 | Example 8 |
|---|---|---|---|---|---|
| Ascorbic acid precipitation after 4 weeks at 4° C. | ○ | ○ | ○ | ○ | ○ |

It turns out that the external compositions of these Examples can have ascorbic acid formulated therein, such that the ascorbic acid is stable also during storage at low temperature, as compared with the external compositions of the Comparative Examples. This reveals that the diols having 3 carbon atoms contribute to the suppression of ascorbic acid precipitation at low temperature.

Tables 4 to 5 below show the results of the stability test (test for confirmation of coloring suppression) for external compositions of Examples and Comparative Examples after storage at 40° C.

TABLE 4

| Component name | | Example 1 | Comparative Example 3 |
|---|---|---|---|
| Ascorbic acid | | 15 | 15 |
| Propylene glycol | | 60 | — |
| Trimethylglycine | | 1.5 | 1.5 |
| Purified water | | 18.5 | 18.5 |
| Dipropylene glycol | | — | 60 |
| Anhydrous ethanol | | 5 | 5 |
| Total | | 100 | 100 |
| 2 W 40° C. | Stability | ○ | x |
| | Δb* ratio | 1 | 2.01 |

TABLE 5

| Component name | | Example 1 | Comparative Example 5 | Comparative Example 6 |
|---|---|---|---|---|
| Ascorbic acid | | 15 | 15 | 15 |
| Propylene glycol | | 60 | 30 | — |
| Trimethylglycine | | 1.5 | 1.5 | 1.5 |
| Purified water | | 18.5 | 18.5 | 18.5 |
| Ethoxydiglycol | | — | 30 | 60 |
| Anhydrous ethanol | | 5 | 5 | 5 |
| Total | | 100 | 100 | 100 |
| 2 W 40° C. | Stability | ○ | Δ | x |
| | Δb* ratio | 1 | 1.43 | 2.05 |

The compositions of these Examples had an effect of coloring suppression and exhibited superior stability for a long period of time, even when stored under high temperature conditions.

Accordingly, it is found that the external compositions represented by these Examples have simultaneously achieved both properties of suppressing the precipitation of ascorbic acid and suppressing the coloring thereof, and in addition, are also superior in the transdermal absorbability of ascorbic acid.

Further, the external compositions of the Examples shown in Table 6 below were prepared by changing the concentration of ascorbic acid, and subjected to the test for confirmation of transdermal absorbability of ascorbic acid. Table 6 shows calculated ratios of transdermal absorbabilities when the test was performed with a composition having the same composition and on one of the same subjects as in the case of Example 1 and the value from the test result of the composition was set to be 1.

TABLE 6

| Component name | Reference Example | Example 9 | Example 10 | Example 11 | Example 12 |
|---|---|---|---|---|---|
| Ascorbic acid | 15 | 3 | 3 | 25 | 25 |
| Propylene glycol | 60 | — | 35.25 | — | 17 |
| 1,3-Propanediol | — | 70.5 | 35.25 | 34.0% | 17 |
| Trimethylglycine | 1.5 | 1.5 | 1.5 | 5 | 5 |
| PEG400 | — | — | — | 5 | 5 |
| Ethylascorbic acid | — | — | — | 1 | 1 |
| Purified water | 18.5 | 20 | 20 | 25 | 25 |
| Anhydrous ethanol | 5 | 5 | 5 | 5 | 5 |
| Total | 100 | 100 | 100 | 100 | 100 |
| Transdermal absorbability (4th to 7th tape strips) (ratio) N = 1 | 1 | 0.42 | 0.39 | 5.7 | 4.8 |

Good transdermal absorption which was in proportion to the concentration of ascorbic acid was observed for the compositions of Examples 9 and 10 having a formula close to that in Example 1 except that the concentration of ascorbic acid was 3%. Also in the compositions of Examples 11 and 12 in which ascorbic acid was formulated at a high concentration of 25%, there was observed good transdermal absorption which was more than proportional to the concentration of ascorbic acid in Example 1. From these results, it has turned out that the external compositions of the Examples in which the diol having 3 carbon atoms was formulated were superior in the transdermal absorbability of ascorbic acid.

Examples 13 to 15 and Comparative Examples 7 to 10

External compositions having ethoxydiglycol formulated therein were further prepared and subjected to the transdermal absorbability test 1. The results are shown in the table below.

TABLE 7

| Component name | Example 13 | Comparative Example 7 |
|---|---|---|
| Ascorbic acid | 10 | 10 |
| Propylene glycol | 62 | 12 |
| 1,3-Propanediol | — | — |
| Dipropylene glycol | — | — |
| Trimethylglycine | 3 | 3 |
| PEG400 | — | — |
| Ethoxydiglycol | — | 50 |
| Purified water | 20 | 20 |
| Anhydrous ethanol | 5 | 5 |
| Total | 100 | 100 |
| Transdermal absorbability (1th to 7th tape strips) (ratio) N = 1 | 1.38 | 1 |

From these results, it has turned out that the external composition having a high concentration of propylene glycol formulated therein was superior in the transdermal absorbability of ascorbic acid to that having a high concentration of ethoxydiglycol formulated therein.

The test for confirmation of coloring suppression was further performed, in order to verify the change in the coloring suppression effect in terms of the amount of ethoxydiglycol. The results are shown in the table below.

TABLE 8

| Component name | Example 14 | Example 15 | Comparative Example 8 | Comparative Example 9 | Comparative Example 10 |
|---|---|---|---|---|---|
| Ascorbic acid | 10 | 10 | 10 | 10 | 10 |
| Purified water | 10 | 10 | 10 | 10 | 10 |
| 1,3-Propanediol | 70 | 60 | 40 | 30 | 10 |
| Trimethylglycine | 1 | 1 | 1 | 1 | 1 |
| Anhydrous ethanol | 9 | 9 | 9 | 9 | 9 |
| Ethoxydiglycol | — | 10 | 30 | 40 | 60 |
| Total | 100 | 100 | 100 | 100 | 100 |
| pH | 4.01 | 4.01 | 4.04 | 4.02 | 3.87 |
| 1 W (50° C.) Stability | ○ | ○ | △ | x | x |
| Δb* ratio | 1.0 | 1.12 | 1.52 | 1.91 | 2.67 |

From these results, it has turned out that the external compositions having less than 30% of ethoxydiglycol formulated therein exhibited a superior effect of coloring suppression to those having a higher concentration of ethoxydiglycol formulated therein.

Examples 16 to 45 and Comparative Examples 11 to 16

In similar procedures, the test 1 for confirmation of suppression of ascorbic acid precipitation and the test for confirmation of coloring suppression were further performed on external compositions of other Examples and Comparative Examples. The results are shown in each of the tables below.

TABLE 9

| Component name | Example 16 | Example 17 | Example 18 | Example 19 | Example 20 | Example 21 | Comparative Example 11 |
|---|---|---|---|---|---|---|---|
| Ascorbic acid | 15 | 15 | 15 | 15 | 15 | 15 | 15 |
| Purified water | 17 | 17 | 17 | 17 | 17 | 17 | 17 |
| Anhydrous ethanol | 8 | 8 | 8 | 8 | 8 | 8 | 8 |
| 1,3-Propanediol | 59 | 58 | 58 | 58 | 59 | 59 | 60 |
| Trimethylglycine | — | 1 | 1 | 1 | — | — | — |
| Sodium citrate | 1 | 1 | — | — | — | — | — |
| 3-O-ethylascorbic acid | — | — | — | — | — | 1 | — |
| Sodium succinate | — | — | 1 | — | 0.3 | — | — |
| Sodium lactate | — | — | — | 1 | — | — | — |
| Total | 100 | 100 | 100 | 100 | 100 | 100 | 100 |
| 4° C. 1 W | ○ | ○ | ○ | ○ | ○ | ○ | x |
| 4° C. 4 W | ○ | ○ | ○ | ○ | ○ | ○ | x |
| Δb ratio | 1.29 | 1.18 | 1.20 | 1.22 | 1.00 | 0.98 | — |
| Δb ratio | ○ | ○ | ○ | ○ | ○ | ○ | — |
| pH | 4.1 | 4.16 | 4.12 | 4.09 | 3.58 | 3.27 | 2.54 |

From these results, it has turned out that the external compositions of these Examples had both superior stability of ascorbic acid and superior effect of coloring suppression.

In similar procedures, the test 1 for confirmation of ascorbic acid precipitation suppression was further performed on external compositions of other Examples and Comparative Examples. The results are shown in each of the tables below.

TABLE 10

| Component name | Example 22 | Example 23 | Example 24 | Example 25 | Example 26 | Comparative Example 12 |
|---|---|---|---|---|---|---|
| Ascorbic acid | 15 | 15 | 15 | 15 | 15 | 15 |
| Purified water | 18 | 18 | 18 | 18 | 18 | 18 |
| Anhydrous ethanol | 8 | 8 | 8 | 8 | 8 | 8 |
| 1,3-Propanediol | 58.5 | 58.5 | — | — | — | 59 |
| Propylene glycol | — | — | 58.5 | 58.5 | 58.7 | — |
| Sodium citrate | 0.5 | — | 0.5 | — | — | — |
| 3-O-ethylascorbic acid | — | — | — | — | — | — |
| L-Carnitine | — | 0.5 | — | 0.5 | — | — |
| Sodium succinate | — | — | — | — | 0.3 | — |
| | 100 | 100 | 100 | 100 | 100 | 100 |
| 4° C. 1 W | ○ | ○ | ○ | ○ | ○ | x |
| 4° C. 4 W | ○ | ○ | ○ | ○ | ○ | x |
| pH | 3.82 | 3.59 | 3.76 | 3.55 | 3.57 | 2.5 |

TABLE 11

| Component name | Example 27 | Example 28 | Example 29 | Example 30 | Comparative Example 13 | Comparative Example 14 |
|---|---|---|---|---|---|---|
| Ascorbic acid | 15 | 15 | 15 | 15 | 15 | 15 |
| Purified water | 18 | 18 | 18 | 18 | 18 | 18 |
| Anhydrous ethanol | 8 | 8 | 8 | 8 | 8 | 8 |
| 1,3-Propanediol | 58 | 57.7 | 57.7 | 57.7 | — | — |
| 1,3-Butylene glycol | — | — | — | — | 58 | — |
| Dipropylene glycol | — | — | — | — | — | 58 |
| Trimethylglycine | 1 | 1 | 1 | 1 | 1 | 1 |
| Sodium citrate | — | 0.3 | — | — | — | — |
| Sodium pyrosulfite | — | — | — | 0.3 | — | — |
| Sodium succinate | — | — | 0.3 | — | — | — |
| | 100 | 100 | 100 | 100 | 100 | 100 |
| 4° C. 1 W | ○ | ○ | ○ | ○ | x | x |
| 4° C. 4 W | ○ | ○ | ○ | ○ | x | x |
| pH | 3.27 | 3.65 | 3.6 | 3.27 | 3.41 | 3.31 |

TABLE 12

| Component name | Example 31 | Example 32 | Example 33 | Example 34 | Example 35 | Example 36 | Example 37 | Example 38 | Example 39 | Example 40 | Comparative Example 15 |
|---|---|---|---|---|---|---|---|---|---|---|---|
| Ascorbic acid | 15 | 15 | 15 | 15 | 15 | 15 | 15 | 15 | 15 | 15 | 15 |
| Purified water | 18 | 18 | 18 | 18 | 18 | 18 | 18 | 18 | 18 | 18 | 18 |
| Anhydrous ethanol | 8 | 8 | 8 | 8 | 8 | 8 | 8 | 8 | 8 | 8 | 8 |
| 1,3-Propanediol | 57 | 57.5 | 58 | 57.7 | 57.7 | 58.4 | 57.7 | 57.7 | 58.5 | 58.45 | 59 |
| 3-O-ethylascorbic acid | 1 | 0.5 | 0.5 | 1 | 1 | 0.5 | 1 | 1 | 0.5 | 0.5 | — |
| Trimethylglycine | 1 | 1 | 0.5 | — | — | — | — | — | — | — | — |
| Sodium citrate | — | — | — | 0.3 | — | — | — | — | — | — | — |
| L-Carnitine | — | — | — | — | — | — | 0.3 | — | — | — | — |
| L-Arginine | — | — | — | — | — | — | — | 0.3 | — | — | — |
| Sodium pyrosulfite | — | — | — | — | — | — | — | — | — | 0.05 | — |
| Sodium succinate | — | — | — | — | 0.3 | 0.1 | — | — | — | — | — |
|  | 100 | 100 | 100 | 100 | 100 | 100 | 100 | 100 | 100 | 100 | 100 |
| 4° C. 1 W | ○ | ○ | ○ | ○ | ○ | ○ | ○ | ○ | ○ | ○ | x |
| 4° C. 4 W | ○ | ○ | ○ | ○ | ○ | ○ | ○ | ○ | ○ | ○ | x |
| pH | 3.23 | 3.4 | 3.22 | 3.52 | 3.44 | 3.33 | 3.33 | 3.36 | 2.65 | 2.66 | 2.5 |

TABLE 13

| Component name | Example 41 | Example 42 | Example 43 | Example 44 | Example 45 | Comparative Example 16 |
|---|---|---|---|---|---|---|
| Ascorbic acid | 15 | 15 | 15 | 15 | 15 | 15 |
| Purified water | 18 | 18 | 18 | 18 | 18 | 18 |
| Anhydrous ethanol | 8 | 8 | 8 | 8 | 8 | 8 |
| Propylene glycol | 58 | 57.7 | 58.4 | 57.7 | 57.7 | 59 |
| 3-O-ethylascorbic acid | 0.5 | 1 | 0.5 | 1 | 1 | — |
| Trimethylglycine | 0.5 | — | — | — | — | — |
| Sodium citrate | — | 0.3 | — | — | — | — |
| L-Carnitine | — | — | — | 0.3 | — | — |
| L-Arginine | — | — | — | — | 0.3 | — |
| Sodium succinate | — | — | 0.1 | — | — | — |
|  | 100 | 100 | 100 | 100 | 100 | 100 |
| 4° C. 1 W | ○ | ○ | ○ | ○ | ○ | x |
| 4° C. 4 W | ○ | ○ | ○ | ○ | ○ | x |
| pH | 3.24 | 3.42 | 3.29 | 3.28 | 3.25 | 2.49 |

From these results, it has turned out that the external compositions of these Examples had superior stability of ascorbic acid.

Examples 46 to 61 and Comparative Examples 17 to 46

The test 1 for confirmation of suppression of ascorbic acid precipitation and the test for confirmation of coloring suppression were performed on external compositions of additional Examples and Comparative Examples. The results are shown in the table below. Regarding Δb, the Δb value for Example 47 was set to 1.

TABLE 14

| Component name | Example 46 | Example 47 | Example 48 | Example 49 | Example 50 | Example 51 | Comparative Example 17 | Comparative Example 18 |
|---|---|---|---|---|---|---|---|---|
| Ascorbic acid | 10 | 10 | 10 | 10 | 10 | 10 | 10 | 10 |
| Purified water | 15 | 15 | 15 | 15 | 15 | 15 | 15 | 15 |
| Anhydrous ethanol | 8 | 8 | 8 | 8 | 8 | 8 | 8 | 8 |
| 1,3-Propanediol | 66.7 | — | 66.7 | 66.7 | 66.7 | 66.7 | 64.5 | — |
| Ethoxydiglycol | — | — | — | — | — | — | — | — |
| Propylene glycol | — | 66.7 | — | — | — | — | — | — |
| Dipropylene glycol | — | — | — | — | — | — | — | 66.7 |
| Nicotinic acid amide | — | — | — | — | — | — | 2.5 | — |
| Sodium citrate | — | 0.3 | — | — | — | — | — | — |
| 3-O-ethylascorbic acid | 0.3 | — | — | — | — | — | — | — |
| dl-Sodium pyrrolidone-carboxylate | — | — | — | — | 0.3 | — | — | — |

TABLE 14-continued

| Component name | Example 46 | Example 47 | Example 48 | Example 49 | Example 50 | Example 51 | Comparative Example 17 | Comparative Example 18 |
|---|---|---|---|---|---|---|---|---|
| Sodium pyrosulfite | — | — | — | — | — | 0.3 | — | — |
| Sodium lactate | — | — | — | 0.3 | — | — | — | — |
| Sodium succinate | — | — | 0.3 | — | — | — | — | 0.3 |
| | 100 | 100 | 100 | 100 | 100 | 100 | 100 | 100 |
| 4° C. 1 W | ○ | ○ | ○ | ○ | ○ | ○ | x | ○ |
| 4° C. 4 W | ○ | ○ | ○ | ○ | ○ | ○ | x | ○ |
| Δb ratio | 0.71 | 1.13 | 1.00 | 1.02 | 0.99 | 0.58 | 2.45 | 3.52 |
| Stability | ○ | ○ | ○ | ○ | ○ | ○ | x | x |
| pH | 3.13 | 4.21 | 4.48 | 4.49 | 4.37 | 3.99 | 4.13 | 4.45 |

Next, external compositions were prepared in which tranexamic acid, nicotinic acid amide, and triethanolamine, which are compounds containing an amino or amide group, other than the low-molecular-weight betaine; hydroxylated lecithins, magnesium L-ascorbyl phosphate, or others were used instead of the component (B), and compared for their stability to external compositions of Examples. As a stability test, the test 1 for confirmation of ascorbic acid precipitation suppression was performed. The results are shown in the table below.

TABLE 15

| Component name | Comparative Example 19 | Comparative Example 20 | Comparative Example 21 | Comparative Example 22 | Comparative Example 23 | Comparative Example 24 | Comparative Example 25 | Comparative Example 26 | Example 52 |
|---|---|---|---|---|---|---|---|---|---|
| Ascorbic acid | 15 | 15 | 15 | 15 | 15 | 15 | 15 | 15 | 15 |
| Purified water | 18 | 18 | 18 | 18 | 18 | 18 | 18 | 18 | 18 |
| Anhydrous ethanol | 8 | 8 | 8 | 8 | 8 | 8 | 8 | 8 | 8 |
| 1,3-Propanediol | 58 | 56.5 | 58.5 | 58.7 | 58.5 | 58.5 | 58 | 59 | 58 |
| 1,3-Butylene glycol | — | — | — | — | — | — | — | — | — |
| Dipropylene glycol | — | — | — | — | — | — | — | — | — |
| Glycerin | — | — | — | — | — | — | — | — | — |
| NaOH | — | — | — | — | — | — | — | q.s. | — |
| Tranexamic acid | 1 | — | — | — | — | — | — | — | — |
| Nicotinic acid amide | — | 2.5 | — | — | — | — | — | — | — |
| Triethanolamine | — | — | 0.5 | 0.3 | — | — | — | — | — |
| LECINOL WS-50, a mixture of hydroxylated soybean phospholipid and concentrated glycerin | — | — | — | — | 0.5 | — | — | — | — |
| LECINOL SH-50, a mixture of hydroxylated soybean phospholipid and concentrated glycerin | — | — | — | — | — | 0.5 | — | — | — |
| Sodium succinate | — | — | — | — | — | — | — | — | — |
| Sodium lactate | — | — | — | — | — | — | — | — | 1 |
| Sodium citrate | — | — | — | — | — | — | — | — | — |
| L-Carnitine | — | — | — | — | — | — | — | — | — |
| Magnesium L-ascorbyl phosphate | — | — | — | — | — | — | 1 | — | — |
| | 100 | 100 | 100 | 100 | 100 | — | 100 | 100 | 100 |

TABLE 15-continued

| Component name | Comparative Example 19 | Comparative Example 20 | Comparative Example 21 | Comparative Example 22 | Comparative Example 23 | Comparative Example 24 | Comparative Example 25 | Comparative Example 26 | Example 52 |
|---|---|---|---|---|---|---|---|---|---|
| 4° C. 1 W | ○ | x | ○ | ○ | ○ | ○ | x | ○ | ○ |
| 4° C. 4 W | x | x | x | x | x | x | x | x | ○ |
| pH | 4.42 | 3.54 | 4.26 | 4.07 | 3.28 | 3.07 | 3.68 | 3.32 | 4.17 |

Next, external compositions were prepared in which another polyhydric alcohol or the like was used instead of the component (B), and compared with those of Examples for their stability. The results are shown in the table below.

TABLE 16

| Component name | Comparative Example 27 | Comparative Example 28 | Comparative Example 29 | Comparative Example 30 | Comparative Example 31 | Comparative Example 32 | Comparative Example 33 | Comparative Example 34 | Comparative Example 35 | Comparative Example 36 | Comparative Example 37 |
|---|---|---|---|---|---|---|---|---|---|---|---|
| Ascorbic acid | 15 | 15 | 15 | 15 | 15 | 15 | 15 | 15 | 15 | 15 | 15 |
| Purified water | 18 | 18 | 18 | 18 | 18 | 18 | 18 | 18 | 18 | 18 | 18 |
| Anhydrous ethanol | 8 | 8 | 8 | 8 | 8 | 8 | 8 | 8 | 8 | 8 | 66.7 |
| 1,3-Propanediol | — | — | — | — | — | — | — | — | — | — | — |
| 1,3-Butylene glycol | 58.7 | — | 58.5 | 58.5 | 58.7 | — | 58.7 | — | — | — | — |
| Dipropylene glycol | — | 58.7 | — | — | — | 58.7 | — | 58.7 | — | — | — |
| Glycerin | — | — | — | — | — | — | — | — | 58.7 | 58.7 | — |
| NaOH | — | — | — | — | — | — | — | — | — | — | — |
| Tranexamic acid | — | — | — | — | — | — | — | — | — | — | — |
| Nicotinic acid amide | — | — | — | — | — | — | — | — | — | — | — |
| Triethanolamine | — | — | — | — | — | — | — | — | — | — | — |
| LECINOL WS-50, a mixture of hydroxylated soybean phospholipid and concentrated glycerin | — | — | 0.5 | — | — | — | — | — | — | — | — |
| LECINOL SH-50, a mixture of hydroxylated soybean phospholipid and concentrated glycerin | — | — | — | 0.5 | — | — | — | — | — | — | — |
| Sodium succinate | 0.3 | 0.3 | — | — | — | — | — | — | 0.3 | — | 0.3 |
| Sodium lactate | — | — | — | — | — | — | 0.3 | 0.3 | — | — | — |
| Sodium citrate | — | — | — | — | — | — | — | — | — | — | — |
| L-Carnitine | — | — | — | — | 0.3 | 0.3 | — | — | — | 0.3 | — |
| Magnesium L-ascorbyl phosphate | — | — | — | — | — | — | — | — | — | — | — |
| | 100 | 100 | 100 | 100 | 100 | 100 | 100 | 100 | 100 | 100 | 100 |
| 4° C. 1 W | x | x | x | x | x | x | x | x | x | x | x |
| 4° C. 4 W | x | x | x | x | x | x | x | x | x | x | x |
| pH | 3.64 | 3.59 | 3.34 | 3.16 | 3.42 | 3.39 | 3.71 | 3.74 | Insoluble | Insoluble | Insoluble |

TABLE 17

| Component name | Example 53 | Example 54 | Example 55 | Example 56 | Example 57 | Comparative Example 38 | Comparative Example 39 | Comparative Example 40 |
|---|---|---|---|---|---|---|---|---|
| Ascorbic acid | 20 | 20 | 20 | 20 | 20 | 20 | 20 | 20 |
| Purified water | 40 | 40 | 40 | 40 | 40 | 40 | 40 | 40 |
| Anhydrous ethanol | 3 | 3 | 3 | 3 | 3 | 3 | 3 | 3 |
| 1,3-Propanediol | — | 33 | 33 | 33 | 33 | 37 | — | — |
| Propylene glycol | 32 | — | — | — | — | — | — | — |
| 1,3-Butylene glycol | — | — | — | — | — | — | — | 33 |
| Dipropylene glycol | — | — | — | — | — | — | 33 | — |
| Trimethylglycine | 5 | — | — | — | — | — | — | — |
| Sodium citrate | — | — | — | 4 | — | — | — | — |
| 3-O-ethylascorbic acid | — | 4 | — | — | — | — | — | — |
| L-Carnitine | — | — | — | — | 4 | — | — | — |
| Sodium succinate | — | — | 4 | — | — | — | 4 | 4 |
|  | 100 | 100 | 100 | 100 | 100 | 100 | 100 | 100 |
| 4° C. 1 W | ○ | ○ | ○ | ○ | ○ | × | ○ | ○ |
| 4° C. 4 W | ○ | ○ | ○ | ○ | ○ | × | × | × |
| pH | 3.31 | 2.93 | 4.22 | 4.25 | 3.93 | 2.34 | 4.26 | 4.26 |

From these results, it has turned out that the external compositions without the component (B) lead to the precipitation of the ascorbic acid and had a problem in stability.

Next, external compositions containing high concentrations of ascorbic acid were prepared, and compared with those of Examples for their stability. As stability tests, the tests 1 and 2 for confirmation of ascorbic acid precipitation suppression were performed. The results are shown in the tables below.

TABLE 18

| Component name | Example 58 | Comparative Example 41 | Comparative Example 42 | Comparative Example 43 |
|---|---|---|---|---|
| Ascorbic acid | 25 | 25 | 25 | 25 |
| Purified water | 40 | 40 | 40 | 40 |
| Anhydrous ethanol | 8 | 8 | 8 | 8 |
| 1,3-Propanediol | 24.5 | 27 | — | — |
| 1,3-Butylene glycol | — | — | 24.5 | — |
| Dipropylene glycol | — | — | — | 24.5 |
| 3-O-ethylascorbic acid | 2.5 | — | — | — |
| Sodium succinate | — | — | 2.5 | 2.5 |
|  | 100 | 100 | 100 | 100 |
| 4° C. 1 W | ○ | × | × | × |
| 4° C. 4 W | ○ | × | × | × |
| pH | 2.01 | 2.15 | 3.61 | 3.62 |

TABLE 19

| Component name | Example 59 | Example 60 | Example 61 | Comparative Example 44 | Comparative Example 45 | Comparative Example 46 |
|---|---|---|---|---|---|---|
| Ascorbic acid | 25 | 25 | 25 | 25 | 25 | 25 |
| Purified water | 40 | 40 | 40 | 40 | 40 | 40 |
| Anhydrous ethanol | 3 | 3 | 3 | 3 | 3 | 3 |
| 1,3-Propanediol | 27 | 28 | 28 | 32 | — | — |
| 1,3-Butylene glycol | — | — | — | — | 28 | — |
| Dipropylene glycol | — | — | — | — | — | 28 |
| Trimethylglycine | 5 | — | — | — | — | — |
| 3-O-ethyl ascorbic acid | — | 4 | — | — | — | — |
| Sodium succinate | — | — | 4 | — | 4 | 4 |
|  | 100 | 100 | 100 | 100 | 100 | 100 |
| 4° C. 1 W | ○ | ○ | ○ | × | × | × |
| −8° C. 1 W | ○ | ○ | ○ | × | × | × |
| pH | 3.32 | 2.09 | 3.98 | 2.16 | 3.99 | 3.97 |

It has turned out that the external compositions of these Examples containing high concentrations of ascorbic acid also lead to the suppression of the precipitation of the ascorbic acid over time and were superior in stability.

Examples 62 to 70 and Comparative Examples 47 to 54

The tables below show the results of the transdermal absorbability test for external compositions of Examples and Comparative Examples.

The numerical values described in the row describing the results of the transdermal absorbability test for external compositions of Examples are values obtained as ratios relative to the amount of transdermal absorption of ascorbic acid for the composition of Comparative Example 47, which was set to be 1.

Ratio=(transdermal absorption amount for the composition of any of Examples (μg/cm$^2$)/(transdermal absorption amount for the composition of Comparative Example 47(μg/cm$^2$)

Furthermore, regarding these ratios, the numerical values described in the row describing the transdermal absorption of the compositions of Comparative Examples are values obtained as ratios relative to the amount of transdermal absorption of ascorbic acid for the composition of Comparative Example 47, which was set to be 1, as indicated below:

Ratio=(transdermal absorption amount for the composition of any of Comparative Examples (μg/cm$^2$)/(transdermal absorption amount of the composition of Comparative Example 47(μg/cm$^2$).

TABLE 20

| Component name | Example 62 | Example 63 | Comparative Example 47 | Comparative Example 48 |
|---|---|---|---|---|
| Ascorbic acid | 10 | 10 | 10 | 10 |
| Purified water | 15 | 15 | 15 | 15 |
| Anhydrous ethanol | 8 | 8 | 8 | 8 |
| 1,3-Propanediol | 66.7 | 66.7 | — | — |
| Ethoxydiglycol | — | — | — | 66.7 |
| 1,3-Butylene glycol | — | — | 66.7 | — |
| 3-O-ethylascorbic acid | 0.3 | — | — | — |
| Sodium succinate | — | 0.3 | 0.3 | 0.3 |
| Total | 100 | 100 | 100 | 100 |
| pH | 3.13 | 4.48 | 4.45 | 4.05 |
| Transdermal absorbability test (1st to 7th tape strips) (ratio) | 12.06 | 9.07 | 1.00 | 2.48 |

TABLE 21

| Component name | Example 64 | Example 65 | Comparative Example 49 | Comparative Example 50 |
|---|---|---|---|---|
| Ascorbic acid | 20 | 20 | 20 | 20 |
| Purified water | 40 | 40 | 40 | 40 |
| Anhydrous ethanol | 3 | 3 | 3 | 3 |
| 1,3-Propanediol | 33 | 33 | — | — |
| 1,3-Butylene glycol | — | — | — | 33 |
| Dipropylene glycol | — | — | 33 | — |
| 3-O-ethylascorbic acid | 4 | — | — | — |
| Sodium succinate | — | 4 | 4 | 4 |
| Total | 100 | 100 | 100 | 100 |
| pH | 2.93 | 4.22 | 4.26 | 4.26 |
| Transdermal absorbability test (1st to 7th tape strips) (ratio) | 11.92 | 5.77 | 0.97 | 1.00 |

From these results, it has turned out that the external compositions of these Examples were superior in transdermal absorbability, as compared with those of the Comparative Examples.

Next, external compositions of Examples and Comparative Examples were evaluated with respect to a feeling of permeation, the presence or absence of stickiness, the presence or absence of irritation, and the smoothness of the skin. The results obtained are shown the tables below.

TABLE 22

| Component name | Example 66 | Example 67 | Comparative Example 51 | Comparative Example 52 |
|---|---|---|---|---|
| Ascorbic acid | 25 | 25 | 25 | 25 |
| Purified water | 40 | 40 | 40 | 40 |
| Anhydrous ethanol | 3 | 3 | 3 | 3 |
| 1,3-Propanediol | 27 | 28 | — | — |
| 1,3-Butylene glycol | — | — | 28 | — |
| Dipropylene glycol | — | — | — | 28 |
| Trimethylglycine | 5 | — | — | — |
| 3-O-ethylascorbic acid | — | 4 | 4 | 4 |
| Sodium succinate | — | — | — | — |
| | 100 | 100 | 100 | 100 |
| Feeling of penetration | 4 | 4.33 | 2.33 | 2.67 |
| Absence of stickiness | 4 | 4 | 2.33 | 1.33 |
| Absence of irritation | 5 | 5 | 5 | 5 |
| Skin smoothness | 3.33 | 4 | 3 | 2.33 |
| Overall assessment | ◎ | ◎ | Δ | X |
| pH | 3.32 | 2.09 | 2.14 | 2.19 |

TABLE 23

| Component name | Example 68 | Example 69 | Example 70 | Comparative Example 53 | Comparative Example 54 |
|---|---|---|---|---|---|
| Ascorbic acid | 10 | 10 | 10 | 10 | 10 |
| Purified water | 15 | 15 | 15 | 15 | 15 |
| Anhydrous ethanol | 8 | 8 | 8 | 8 | 8 |
| 1,3-Propanediol | 66.7 | — | 66.7 | — | — |
| Propylene glycol | — | 66.7 | — | — | — |
| 1,3-Butylene glycol | — | — | — | 66.7 | — |
| Dipropylene glycol | — | — | — | — | 66.7 |
| Sodium citrate | — | 0.3 | — | — | — |
| 3-O-ethylascorbic acid | 0.3 | — | — | 0.3 | 0.3 |
| Sodium succinate | — | — | 0.3 | — | — |
| | 100 | 100 | 100 | 100 | 100 |
| Feeling of penetration | 4.33 | 4.33 | 4.67 | 2.67 | 2.00 |
| Absence of stickiness | 4.33 | 4 | 5 | 2.67 | 1.67 |
| Absence of irritation | 5 | 5 | 5 | 5 | 4.67 |
| Skin smoothness | 4.67 | 4.33 | 4.67 | 3.33 | 3.33 |
| Overall assessment | ◎ | ◎ | ◎ | Δ | X |
| pH | 3.13 | 4.21 | 4.48 | 3.2 | 3.16 |

The external compositions of these Examples were shown to be superior in use feeling.

Formula Examples

Formula examples of the present invention are shown in the tables below. Any of these formula examples can be suitably used for face lotions, serums, and others. The contents of the respective components in the formula examples are all given in mass %.

TABLE 24

| Component name | Formula Example 1 Formulation amount (%) | Formula Example 2 Formulation amount (%) | Formula Example 3 Formulation amount (%) | Formula Example 4 Formulation amount (%) | Formula Example 5 Formulation amount (%) | Formula Example 6 Formulation amount (%) | Formula Example 7 Formulation amount (%) | Formula Example 8 Formulation amount (%) |
|---|---|---|---|---|---|---|---|---|
| Ascorbic acid | 30 | 30 | 30 | 25 | 25 | 25 | 25 | 25 |
| Propylene glycol |  | 8.88 | 11.83 | 10.84 | 22.18 | 19.08 | 13.14 |  |
| 1,3-Propanediol | 30.35 | 30 | 30 | 40 | 30 | 30 | 30 | 35.63 |
| Polyethylene glycol 400 |  |  |  |  |  |  | 5 |  |
| 1,3-Butylene glycol | 0.5 |  |  |  |  |  |  |  |
| Dipropylene glycol |  |  |  |  | 1 |  |  |  |
| Concentrated glycerin |  |  |  |  |  |  |  |  |
| Anhydrous ethanol | 2 | 2 |  |  |  | 3 | 3 | 15 |
| Trimethylglycine | 4.5 |  | 1 |  |  |  |  |  |
| L-carnitine |  |  |  |  |  |  |  | 0.5 |
| 3-O-Ethylascorbic acid |  | 0.5 | 0.3 | 0.3 | 0.3 |  |  |  |
| Sodium citrate |  |  |  |  |  | 2 |  |  |
| Sodium succinate |  |  |  |  | 0.15 |  | 2 |  |
| Sodium lactate |  |  |  |  |  |  |  |  |
| Sodium dl-pyrrolidonecarboxylate |  |  |  |  |  |  |  | 2 |
| Purified water | 32 | 28 | 25 | 22 | 20 | 20 | 20 | 20 |
| Polyoxyethylene hydrogenated castor oil 40 |  |  |  |  |  | 0.2 |  |  |
| Polyoxyethylene (20) polyoxypropylene (4) cetyl ether |  |  | 0.2 | 0.2 | 0.4 |  |  |  |
| Polyoxyethylene polyoxypropylene decyl tetradecyl ether | 0.2 | 0.2 |  |  |  |  | 0.2 | 0.5 |
| Jojoba oil |  |  |  |  | 0.1 |  |  |  |
| d-δ-Tocopherol | 0.1 | 0.1 | 0.1 | 0.1 | 0.1 | 0.1 | 0.1 | 0.1 |
| dl-α-Tocopherol acetate |  |  |  |  |  |  |  |  |
| Grapefruit fruit extract |  |  | 0.5 | 0.5 | 0.1 | 0.1 | 0.5 | 0.5 |
| Lemon extract | 0.1 |  | 0.5 | 0.5 | 0.1 | 0.1 | 0.5 | 0.5 |
| Kiwi extract | 0.1 |  | 0.1 | 0.1 | 0.1 | 0.1 | 0.1 | 0.1 |
| Artichoke extract | 0.1 |  | 0.1 | 0.1 | 0.1 |  | 0.1 | 0.1 |
| Flavor |  | 0.3 | 0.3 | 0.3 | 0.3 | 0.3 | 0.3 |  |
| Dipotassium glycyrrhizate | 0.05 |  | 0.05 | 0.05 | 0.05 |  | 0.05 | 0.05 |
| Hydrolyzed hyaluronic acid |  | 0.01 | 0.01 |  | 0.01 | 0.01 |  | 0.1 |
| Na hyaluronate |  | 0.01 | 0.01 | 0.01 | 0.01 | 0.01 | 0.01 | 0.01 |
|  | 100 | 100 | 100 | 100 | 100 | 100 | 100 | 100 |

| Component name | Formula Example 9 Formulation amount (%) | Formula Example 10 Formulation amount (%) | Formula Example 11 Formulation amount (%) | Formula Example 12 Formulation amount (%) | Formula Example 13 Formulation amount (%) | Formula Example 14 Formulation amount (%) | Formula Example 15 Formulation amount (%) |
|---|---|---|---|---|---|---|---|
| Ascorbic acid | 20 | 20 | 20 | 20 | 20 | 20 | 20 |
| Propylene glycol | 25.33 | 23.08 | 25.14 | 16.93 | 28.08 | 32.94 |  |
| 1,3-Propanediol | 30 | 30 | 20 | 20 | 20 | 20 | 58.13 |
| Polyethylene glycol 400 |  |  |  |  | 2 |  |  |
| 1,3-Butylene glycol |  |  | 2 |  |  |  |  |
| Dipropylene glycol | 1 |  |  |  |  | 2 |  |
| Concentrated glycerin | 0.5 |  | 5 |  |  |  |  |
| Anhydrous ethanol | 3 | 3 | 5 | 10 |  | 5 |  |
| Trimethylglycine |  |  |  |  | 3 |  |  |
| L-carnitine |  |  |  |  |  | 3 |  |
| 3-O-Ethylascorbic acid | 0.3 |  |  | 0.2 |  |  |  |
| Sodium citrate |  |  |  |  |  |  | 0.5 |
| Sodium succinate |  |  |  |  |  |  |  |
| Sodium lactate |  | 2 |  |  |  |  |  |
| Sodium dl-pyrrolidonecarboxylate |  |  | 0.8 | 1 |  |  |  |

TABLE 24-continued

| | | | | | | | |
|---|---|---|---|---|---|---|---|
| Purified water | 18 | 20 | 20 | 30 | 25 | 15 | 18 |
| Polyoxyethylene hydrogenated castor oil 40 | | | | | | | |
| Polyoxyethylene (20) polyoxypropylene (4) cetyl ether | 0.2 | 0.2 | 0.4 | 0.2 | 0.2 | 0.4 | 0.2 |
| Polyoxyethylene polyoxypropylene decyl tetradecyl ether | | | | | | | |
| Jojoba oil | | 0.05 | | | 0.05 | | |
| d-δ-Tocopherol | 0.1 | | 0.1 | 0.1 | | 0.1 | 0.1 |
| dl-α-Tocopherol acetate | | 0.1 | | | 0.1 | | |
| Grapefruit fruit extract | 0.5 | 0.5 | 0.5 | 0.5 | 0.5 | 0.5 | 0.5 |
| Lemon extract | 0.5 | 0.5 | 0.5 | 0.5 | 0.5 | 0.5 | 0.5 |
| Kiwi extract | 0.1 | 0.1 | 0.1 | 0.1 | 0.1 | 0.1 | 0.1 |
| Artichoke extract | 0.1 | 0.1 | 0.1 | 0.1 | 0.1 | 0.1 | 0.1 |
| Flavor | 0.3 | 0.3 | 0.3 | 0.3 | 0.3 | 0.3 | 0.3 |
| Dipotassium glycyrrhizate | 0.05 | 0.05 | 0.05 | 0.05 | 0.05 | 0.05 | 0.05 |
| Hydrolyzed hyaluronic acid | 0.1 | 0.1 | 0.1 | 0.1 | 0.1 | 0.1 | 0.1 |
| Na hyaluronate | 0.1 | 0.1 | | 0.1 | 0.1 | | 0.1 |
| | 100 | 100 | 100 | 100 | 100 | 100 | 100 |

TABLE 25

| Component name | Formula Example 16 Formulation amount (%) | Formula Example 17 Formulation amount (%) | Formula Example 18 Formulation amount (%) | Formula Example 19 Formulation amount (%) | Formula Example 20 Formulation amount (%) | Formula Example 21 Formulation amount (%) | Formula Example 22 Formulation amount (%) | Formula Example 23 Formulation amount (%) |
|---|---|---|---|---|---|---|---|---|
| Ascorbic acid | 20 | 20 | 15 | 15 | 15 | 15 | 15 | 10 |
| Propylene glycol | 37.57 | 31.94 | 25.43 | 23.03 | 47.03 | 13.83 | 1.63 | 14.63 |
| 1,3-Propanediol | 20 | 20 | 30 | 35 | 20 | 25 | 10 | 50 |
| Polyethylene glycol 400 | | 3 | | | | 10 | 30 | |
| 1,3-Butylene glycol | | | | | | | 5 | 5 |
| Dipropylene glycol | | | 3 | | | 10 | 15 | |
| Concentrated glycerin | | | | 2 | | | | |
| Anhydrous ethanol | 2 | 1 | 5 | 5 | | 5 | 5 | 10 |
| Trimethylglycine | | | | | | 1 | 0.5 | |
| L-carnitine | | | | | | | 0.5 | |
| 3-O-Ethylascorbic acid | 0.1 | 2 | | | | 1 | 0.5 | |
| Sodium citrate | | | | | | | | |
| Sodium succinate | 0.5 | | 0.3 | | | | | |
| Sodium lactate | | | | 0.3 | | | | |
| Sodium dl-pyrrolidonecarboxylate | | | | | 0.8 | | | 0.1 |
| Purified water | 18 | 20 | 20 | 18 | 15 | 18 | 15 | 10 |
| Polyoxyethylene hydrogenated castor oil 40 | | | 0.2 | 0.2 | | | | |
| Polyoxyethylene (20) polyoxypropylene (4) cetyl ether | 0.2 | 0.4 | | 0.2 | 0.3 | | | |
| Polyoxyethylene polyoxypropylene decyl tetradecyl ether | | | 0.2 | | | 0.2 | 0.2 | 0.2 |
| Jojoba oil | 0.05 | | | | 0.2 | | | |
| d-δ-Tocopherol | | 0.1 | 0.1 | 0.1 | | 0.1 | 0.1 | |
| dl-α-Tocopherol acetate | 0.1 | | | | 0.1 | 0.1 | | |
| Grapefruit fruit extract | 0.5 | 0.5 | 0.1 | 0.5 | 0.5 | 0.1 | 0.5 | |
| Lemon extract | 0.5 | 0.5 | 0.1 | 0.5 | 0.5 | 0.1 | 0.5 | |
| Kiwi extract | 0.1 | 0.1 | 0.1 | | 0.1 | 0.1 | 0.1 | |
| Artichoke extract | 0.1 | 0.1 | 0.1 | 0.1 | 0.1 | 0.1 | 0.1 | |

TABLE 25-continued

| Component name | | | | | | | | |
|---|---|---|---|---|---|---|---|---|
| Flavor | 0.3 | 0.3 | 0.3 | | 0.3 | 0.3 | 0.3 | |
| Dipotassium glycyrrhizate | 0.05 | 0.05 | 0.05 | 0.05 | 0.05 | 0.05 | 0.05 | 0.05 |
| Hydrolyzed hyaluronic acid | 0.01 | 0.01 | 0.01 | 0.01 | 0.01 | 0.01 | 0.01 | 0.01 |
| Na hyaluronate | 0.01 | | 0.01 | 0.01 | 0.01 | 0.01 | 0.01 | 0.01 |
| | 100 | 100 | 100 | 100 | 100 | 100 | 100 | 100 |

| Component name | Formula Example 24 Formulation amount (%) | Formula Example 25 Formulation amount (%) | Formula Example 26 Formulation amount (%) | Formula Example 27 Formulation amount (%) | Formula Example 28 Formulation amount (%) | Formula Example 29 Formulation amount (%) | Formula Example 30 Formulation amount (%) |
|---|---|---|---|---|---|---|---|
| Ascorbic acid | 10 | 10 | 10 | 5 | 3 | 3 | 3 |
| Propylene glycol | 55.22 | 42.68 | 25.62 | 38.63 | 34.33 | 183.03 | 18.72 |
| 1,3-Propanediol | | 25 | 15 | 15 | 30 | 40 | 40 |
| Polyethylene glycol 400 | 5 | | 15 | 15 | 5 | | |
| 1,3-Butylene glycol | 5 | | 8 | 10 | 11 | 10 | 10 |
| Dipropylene glycol | | | 4 | | 5 | 5 | 5 |
| Concentrated glycerin | | | 0.5 | | | 2.5 | 2.5 |
| Anhydrous ethanol | 15 | 8 | 8 | 10 | 10 | 10 | 10 |
| Trimethylglycine | | | | | | | |
| L-carnitine | | 0.5 | | | | | |
| 3-O-Ethylascorbic acid | | 0.5 | 0.01 | | | | |
| Sodium citrate | | | | | | 0.2 | |
| Sodium succinate | | | | 0.01 | 0.01 | | |
| Sodium lactate | 0.01 | | | | | | |
| Sodium dl-pyrrolidonecarboxylate | | | | | | | |
| Purified water | 8 | 12 | 12 | 5 | | 10 | 10 |
| Polyoxyethylene hydrogenated castor oil 40 | | | | | 0.2 | 0.2 | 0.2 |
| Polyoxyethylene (20) polyoxypropylene (4) cetyl ether | | 0.2 | 0.2 | 0.4 | | | 0.2 |
| Polyoxyethylene polyoxypropylene decyl tetradecyl ether | 0.2 | | | | 0.2 | 0.2 | |
| Jojoba oil | | | | 0.1 | | | |
| d-δ-Tocopherol | | 0.1 | 0.1 | | 0.1 | 0.1 | 0.1 |
| dl-α-Tocopherol acetate | | | | 0.1 | | | |
| Grapefruit fruit extract | 0.5 | | 0.5 | 0.1 | | 0.1 | 0.1 |
| Lemon extract | 0.5 | 0.5 | 0.5 | 0.1 | 0.5 | 0.1 | 0.01 |
| Kiwi extract | 0.1 | 0.1 | 0.1 | 0.1 | 0.1 | 0.1 | |
| Artichoke extract | 0.1 | 0.1 | 0.1 | 0.1 | 0.1 | 0.1 | 0.1 |
| Flavor | 0.3 | 0.3 | 0.3 | 0.3 | 0.3 | 0.3 | |
| Dipotassium glycyrrhizate | 0.05 | | 0.05 | 0.05 | 0.05 | 0.05 | 0.05 |
| Hydrolyzed hyaluronic acid | 0.01 | 0.01 | 0.01 | 0.01 | 0.01 | 0.01 | 0.01 |
| Na hyaluronate | 0.01 | 0.01 | 0.01 | | 0.01 | 0.01 | 0.01 |
| | 100 | 100 | 100 | 100 | 100 | 100 | 100 |

The invention claimed is:

1. An external composition, comprising:
   (A) at least one selected from the group consisting of an ascorbic acid and an ascorbic salt in an amount of 1 mass % to 40 mass %;
   (B) 25 mass % or more of a diol having 3 carbon atoms;
   (C) at least one low-molecular-weight betaine in an amount of 0.01 mass % to 10 mass %; and
   (D) 5 to 40 mass % of water,
   and a content of ethoxydiglycol is 0 to 10 mass %.

2. The external composition according to claim 1, wherein the component (D) is in an amount of 0.01 to 20 parts by mass relative to 1 part by mass of the total content of the component (A).

3. The external composition according to claim 1, wherein the component (C) is trimethylglycine.

4. The external composition according to claim 1, wherein the component (B) is 1,3-propanediol or propylene glycol.

5. The external composition according to claim 1, wherein the ascorbic acid or salt thereof is in a concentration of 3 to 30 mass %.

6. The external composition according to claim 1, further comprising (E) a lower alcohol.

7. The external composition according to claim 1, wherein the external composition is substantially free from ethoxydiglycol.

8. The external composition according to claim 1, wherein the external composition is one that is a solubilized system having a transmittance of 85 to 100% at a wavelength of 700 nm.

9. The external composition according to claim 1, wherein the external composition is for promoting the transdermal absorption of the ascorbic acid.

10. A method of imparting stability to an external composition including (A) at least one selected from the group consisting of an ascorbic acid and an ascorbic salt, wherein the method includes using in combination (A) at least one selected from the group consisting of ascorbic acid and an ascorbic salt in an amount of 1 mass % to 40 mass %, (B) 25 mass % or more of a diol having 3 carbon atoms, (C) at least one low-molecular-weight betaine in an amount of 0.01 mass % to 10 mass %, and (D) 5 to 40 mass % of water, and a content of ethoxydiglycol of said composition is 0 to 10 mass %.

* * * * *